United States Patent [19]

Yokota et al.

[11] 4,146,396
[45] Mar. 27, 1979

[54] METHOD OF FORMING COLOR PHOTOGRAPHIC IMAGES

[75] Inventors: Yukio Yokota; Toshiaki Aono; Takeshi Hirose, all of Minami-ashigara, Japan

[73] Assignee: Fuji Photo Film Co., Ltd., Minami-ashigara, Japan

[21] Appl. No.: 762,225

[22] Filed: Jan. 24, 1977

[30] Foreign Application Priority Data

Jan. 26, 1976 [JP] Japan .................................. 51-7770

[51] Int. Cl.² .......................... G03C 7/00; G03C 1/40
[52] U.S. Cl. ...................................... 96/56.2; 96/56.3; 96/56.5; 96/100 N
[58] Field of Search ................ 96/100, 55, 56.5, 56.2, 96/56.3, 56.4

[56] References Cited

U.S. PATENT DOCUMENTS

| | | | |
|---|---|---|---|
| 3,227,551 | 1/1966 | Barr et al. | 96/100 |
| 3,620,747 | 11/1971 | Marchant et al. | 96/100 |
| 3,839,044 | 10/1974 | Salminen et al. | 96/100 |
| 4,009,038 | 2/1977 | Arai et al. | 96/100 |

*Primary Examiner*—Richard L. Schilling

*Attorney, Agent, or Firm*—Sughrue, Rothwell, Mion, Zinn and Macpeak

[57] ABSTRACT

A two equivalent yellow, magenta or cyan coupler having various superior properties and suitable for use in color photographic systems and having a releasable group represented by the following general formula:

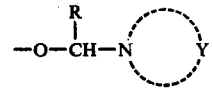

wherein R represents a hydrogen atom, a halogen atom, an alkyl group, an alkenyl group, an aralkyl group, an aralkenyl group, an aryl group or a heterocyclic group; and Y represents the non-metallic atoms necessary to form a 5- to 7-membered ring together with the N atom forming a part thereof, a photographic light-sensitive material containing the two equivalent coupler and a method of forming color photographic images which comprises developing an imagewise exposed silver halide photographic emulsion with an aromatic primary amine developing agent in the presence of the two equivalent coupler.

25 Claims, No Drawings

METHOD OF FORMING COLOR PHOTOGRAPHIC IMAGES

BACKGROUND OF THE INVENTION

1. FIELD OF THE INVENTION

The present invention relates to a novel photographic color coupler, a photographic light-sensitive material containing such a coupler and a method of forming an image using such a coupler.

2. DESCRIPTION OF THE PRIOR ART

It is well known that an oxidized aromatic primary amine developing agent reacts with a dye forming coupler to form a color image by color development after exposure of a silver halide photographic light-sensitive material to light. In this method, a color reproduction process according to the conventional subtractive method is employed to form a cyan, magenta or yellow color image which is in a complementary relation with the red, green or blue color. For instance, a phenol derivative or a naphthol derivative is used as a coupler for forming a cyan color image. The reaction of a coupler with a color developing agent is carried out at the active position of the coupler. Couplers having hydrogen atoms at the active position are four equivalent couplers, that is, they theoretically stoichiometrically require four moles of exposed silver halide as an oxidizing agent for the formation of one mole of dye. On the other hand, couplers having a group capable of being released as an anion at the active position of the coupler are two equivalent couplers, that is, they require only two moles of exposed silver halide for the formation of one mole of dye. Such two equivalent couplers generally provide advantages in comparison with four equivalent couplers. For example, the sharpness of the color images formed is improved. Further, the processing time of the light-sensitive material is reduced because of the decrease in the thickness of the emulsion layer due to the reduction in the amount of silver halide in the emulsion layer. Examples of such releasable groups are a sulfonamido group as described in U.S. Pat. No. 3,737,316, an imido group as described in U.S. Pat. No. 3,749,735, a sulfonyl group as described in U.S. Pat. No. 3,662,328, an aryloxy group as described in U.S. Pat. No. 3,476,563, an acyloxy group as described in U.S. Pat. No. 3,311,476 and a thiocyano group as described in U.S. Pat. No. 3,214,437.

Further, appropriate modifications of the releasable group are also known. For example, a coupler having a releasable group including a diffusible dye moiety is useful in a diffusion transfer process in which a diffusible dye released from the coupler is used to form a dye image in an image receiving layer. Such couplers are designated diffusible dye releasing couplers and are described, for example, in U.S. Pat. Nos. 3,227,550 and 3,765,886, U.S. Patent Defensive Publication T 900,029 and British Pat. No. 1,330,524.

Furthermore, certain colored two equivalent couplers have masking effects for color correction of dye images. Such couplers are designated colored couplers and are described, for example, in U.S. Pat. No. 3,476,563.

Further, a two equivalent coupler which releases a compound having development inhibiting effects is designated a development inhibitor releasing coupler (DIR Coupler). Such a coupler controls development in proportion to the extent of development and thus is effective in reducing the graininess of the developed image, controlling the gradation of the image and improving the color reproducibility. Also, such as coupler can be used in a diffusion transfer process using the effects thereof on an adjacent layer. Examples of such couplers are described in U.S. Patent 3,227,554, Japanese Patent Application (OPI) 122,335/1974 and German Patent Application (OLS) 2,414,006.

As described above, two equivalent couplers have substantial advantages and various applications in comparison with four equivalent couplers, and, thus, they are used to a greater extent.

However, most two equivalent couplers which are known have the disadvantages that their coupling reactivity is insufficient, marked color fog is produced, dispersibility is poor (resulting in difficulties in coating), the coupler per se is unstable and cannot be stored for long periods of time, the stability during storage of color images formed therefrom on color development is poor and the like. Therefore, overcoming such disadvantages has been desired.

Further, when the DIR couplers described in U.S. Pat. No. 3,227,554 are used, during color development, strong development inhibiting effects occur only at a developing center of the silver halide (an aggregate of latent image nuclei) and which are very effective for reducing the graininess of image. On the other hand, they have defects such as decreasing gradation (gamma) and decreasing maximum color density ($D_{max}$) and do not provide interlayer effects which are desirable for color reproduction in multilayer color light-sensitive materials.

Therefore, couplers which have appropriate development inhibiting effects in a layer and can provide strong interlayer effects have been desired from the standpoint of color reproduction.

Furthermore, most couplers described in U.S. Pat. No. 3,227,554 are unstable and thus greater attention must be paid during the production of the color light-sensitive materials and storage of fresh light-sensitive materials.

SUMMARY OF THE INVENTION

An object of the present invention is to provide a novel two equivalent coupler free from the disadvantages which the prior art couplers have.

Another object of the present invention is to provide a method of forming color images on developing a silver halide emulsion in the presence of a novel two equivalent coupler.

A further object of the present invention is to provide a silver-halide color photographic light-sensitive material containing a novel two equivalent coupler and to provide a method of photographic processing using such a novel two equivalent coupler.

As a result of various intensive investigations, it has now been found that the above-described objects are effectively achieved with a photographic two equivalent color forming coupler in which a hydrogen atom at the coupling position capable of coupling with an oxidation product of an aromatic primary amine developing agent is replaced by a group releasable on coupling and represented by the following general formula:

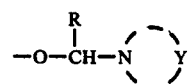

wherein R represents a hydrogen atom, a halogen atom, an alkyl group, an alkenyl group, an aralkyl group, an aralkenyl group, an aryl group or a heterocyclic group; Y represents the nonmetallic atoms necessary to form a 5- to 7-membered ring together with the N atom forming a part thereof.

DETAILED DESCRIPTION OF THE INVENTION

The coupler according to the present invention possesses various functions depending on an appropriate selection of the releasable group. This is, certain couplers release, upon coupling, releasable groups which act on silver halide grains which are being developed or adjacent silver halide grains which are not yet developed and accelerate development, and thus can provide high sensitivity, high gradation and high maximum density and can provide sufficiently high maximum density even in a short period of developing time. Therefore, these couplers are suitable not only in conventional processing steps but also in rapid processing steps. Further, certain couplers are useful as a colored coupler or in a diffusion transfer process. Furthermore, certain couplers can be used as a DIR coupler which exhibits both intralayer effects and interlayer effects.

Preferred couplers of the present invention include, for example, couplers represented by the following general formula (I):

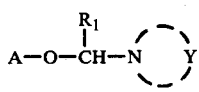
(I)

wherein A represents a coupler residue, for example, a residue of a four equivalent coupler used in a color light-sensitive material in which one hydrogen atom at the active position is eliminated.

As a yellow color image forming coupler residue, a coupler residue A of a pivaloylacetanilide type, a benzoylacetanilide type, a malondiamide type, etc., are preferred.

As a magenta color image forming coupler residue, a coupler residue A having a 5-oxo-2-pyrazoline nucleus or a pyrazolo-[1,5-a]-benzimidazole nucleus is preferred.

As a cyan color image forming coupler residue, a coupler residue A of a 2-acylaminophenol type or an α-naphthol type is preferred.

$R_1$ represents a hydrogen atom, a halogen atom (e.g., a fluorine atom, a chlorine atom or a bromine atom), or has up to 18 carbon atoms and represents an alkyl group (e.g., a methyl, nonyl, isobutyl, cyclohexyl, trichloromethyl, octadecyl, etc., group), an alkenyl group (e.g., a vinyl, allyl, isopropenyl, etc., group), an aralkyl group (e.g., a benzyl, etc., group), an aralkenyl group (e.g., a styryl, etc., group), an aryl group (e.g., a phenyl, p-chlorophenyl, p-nitrophenyl, o- or p-hydroxyphenyl, etc., group), or represents a heterocyclic group having 5- or 6-membered ring containing as a hetero atom, one or more of a nitrogen atom, a sulfur atom or an oxygen atom, for example, a pyridyl group, a thiazolyl group, an imidazolyl group, a pyrimidyl group, an oxazolyl group, etc. The above-described alkyl groups, alkenyl groups, aryl groups or heterocyclic groups include those substituted with one or more substituent(s), e.g., a halogen atom (e.g., a fluorine atom, a chlorine atom or a bromine atom), a nitro group, a cyano group, a hydroxy group, a carboxy group, etc. Further, these groups can be substituted with other conventional substituents. The above-described alkyl groups or alkenyl groups can be straight chain or branched chain groups or cyclic groups.

Y represents the non-metallic atoms necessary to form a 5- to 7-membered ring together with the N atom forming a part thereof. The cyclic moiety formed by Y can be selected from, for example, a group which is known as a releasable group of two equivalent couplers such as a cyclic imide compound as described in Japanese Patent Application (OPI) 26,133/1972, 73,147/1973, 6,341/1975 and 66,834/1973, Japanese Patent Publication No. 29,432/1973, Japanese Patent Application (OPI) 104,026/1975, Japanese Patent Application (OPI) 102,636/1976 Japanese Pat. Application (OPI) No. 3,631/1976, U.S. Pat. Nos. 3,458,315 and 3,730,722, a cyclic amide compound including a lactam compound and a cyclic urea compound as described in Japanese Patent Application (OPI) No. 1,229/1974, 10,736/1974, 28,834/1975 and 34,232/1975, an imidazole compound, a pyrazole compound and a triazole compound described in Japanese Patent Application (OPI) No. 122,335/1974 (corresponding to U.S. Pat. No. 3,933,500) and Japanese Patent Application (OPI) No. 34,232/1974, Japanese Patent Application No. 135,310/1975, a sultam compound, a cyclic amine such as piperidine, piperazine, pyrrolidine, pyrroline, pyrrole, morpholine, pyrazolidine, pyrazoline, etc., and a cyclic moiety represented by the following general formula:

The cyclic moiety of the above-described general formula represents a 5-membered cyclic moiety derived from compounds such as imidazoline-2-thione, imidazolidin-2-thione, oxazolin-2-thione, oxazolidine-2-thione, thiazolin-2-thione, thiazolidin-2-thione, 1,2,3-triazolin-4-thione, 1,2,4-triazolin-3-thione, tetrazolin-5-thione, 1,3,4-oxadiazolin-2-thione, 1,3,4-thiodiazolin-2-thione, pyrazolin-3-thione, etc., or a 6-membered cyclic moiety such as α-thiopyridone, γ-thiopyridone, dihydropyrimidin-4-thione, tetrahydropyrimidin-2-thione, dihydropyrimidin-4-thione, tetrahydropyrimidin-4-thione, dihydropyridazin-3-thione, etc.

The cyclic moiety in the general formula (I) can be a monocyclic ring or a fused ring with another ring. Examples of rings which can be fused therewith include an aromatic ring such as benzene, pyridine, pyrimidine, pyrazine, furan, etc. Further, a fused ring in which an alkylene linkage is bonded to appropriate positions on the cyclic compound can also be used.

Furthermore, the cyclic moiety in the general formula (I) can be a ring having a substituent $R_2$ and represented by the following general formula (II):

(II)

wherein Z has the same meaning as Y defined in the general formula (I); $R_2$ represents a halogen atoms (for example, a fluorine, chlorine, bromine, etc., group), a hydroxy group, a carboxy group, an alkoxycarbonyl group (for example, having 2 to 18 carbon atoms, such as a methoxycarbonyl, ethoxycarbonyl, tetradecyloxycarbonyl, benzyloxycarbonyl, etc., group), a nitro group, a cyano group, an aryl group (for example, a phenyl, naphthyl, pyridyl, furyl, carboxyphenyl, trichlorophenyl, etc., group), an alkoxy group (for example, a methoxy, ethoxy, isopropoxy, benzyloxy, etc., group), an aryloxy group (for example, a phenoxy, chlorophenoxy, carboxyphenoxy, etc., group), an acyl group (for example, an acetyl, benzoyl, tetradecanoyl, 2-(2,4-di-tert-amylphenoxy)butanoyl, etc., group), an acylamino group (for example, an acetamido, dodecanamido, benzamido, perfluorobutanamido, 4-(2,4-di-tert-amylphenoxy)butanamido, etc., group), a sulfo group, a sulfamoyl group (for example, a diethylsulfamoyl, tetradecylsulfamoyl, 3-(2,4-di-tert-amylphenoxy)-propylsulfamoyl, etc., group), a sulfonamido group (for example, a methanesulfonamido, toluenesulfonamido, hexadecanesulfonamido, etc., group), a carbamoyl group (for example, a diethylcarbamoyl, dodecylcarbamoyl, etc., group), an imido group (for example, a succinimido, phthalimido, octadecenylsuccinimido, etc., group), an amino group (for example, an N-substituted benzothiazolin-2-ylamino group represented by the general formula (B):

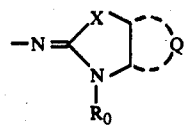
(B)

wherein $R_0$ represents an aliphatic residue, preferably having up to 8 carbon atoms (for example, an alkyl group (such as methyl, ethyl, propyl, butyl, etc.), a substituted alkyl group (such as sulfopropyl, etc.), an alkenyl group, preferably having 2 to 4 carbon atoms (for example, allyl, etc.), etc.), an aralkyl group, preferably having 7 to 12 carbon atoms (for example, benzyl, phenethyl, etc.), or an aryl group, preferably having 6 to 12 carbon atoms (for example, phenyl, etc.); X represents an oxygen atom, a sulfur atom or

Q represents the atoms necessary to form an aromatic ring (for example, a benzene ring which can be substituted with one or more of the above-described substituents, etc.), etc.), a ureido group, a urethane group, an alkylthio group (for example, a methylthio, butylthio, hexadecylthio, etc., group), an amino group (for example, a diethylamino, etc., group) or an alkyl group (for example, a methyl, butyl, tert-amyl, pentadecyl, etc., group).

Of these groups a benzotriazole ring having a group of the general formula (B) described above bonded to the benzene ring thereof is preferred. n represents an integer of 0 to 5, preferably an integer of 0 to 3, depending on Z. When n is 2 or more, $R_2$ can be the same or different.

The releasable group defined hereinbefore is released upon reaction of the coupler with an oxidation product of an aromatic primary amine. Most releasable groups undergo a rapid decomposition as illustrated in the following.

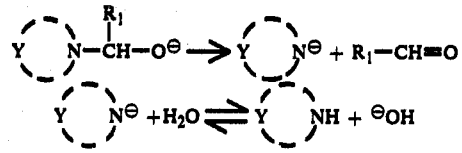

Therefore, when it is desired for a coupler to act imagewise in a certain manner, the purpose can be achieved by selecting a compound which has the desired function as a decomposition product of

The residue represented by A which is particularly useful in the present invention is represented by the following general formulae (III), (IV), (V), (VI) and (VII).

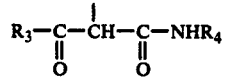
(III)

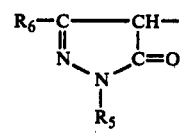
(IV)

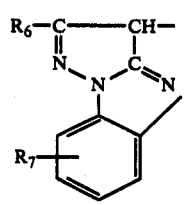
(V)

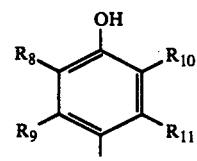
(VI)

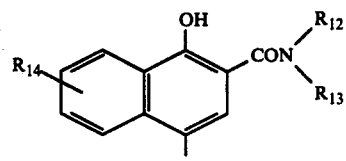
(VII)

In the formula, $R_3$ has preferably up to 32 carbon atoms and represents an aliphatic group, an aromatic group or a heterocyclic group and $R_4$ has preferably 6 to 32 carbon atoms and represents an aromatic group or a heterocyclic group.

The aliphatic group represented by $R_3$ preferably has 1 to 22 carbon atoms, can be unsubstituted or substituted and can be in the form of a chain or cyclic. Preferably $R_3$ is an alkyl group (e.g., a methyl, ethyl, isopropyl, tert-butyl, octyl, hexadecyl, etc., group) which can be unsubstituted or substituted and suitable substituents for the alkyl group include one or more of an alkoxy group (e.g., a methoxy, ethoxy, butoxy, tetradecyloxy, etc., group), an aryloxy group (e.g., a phenoxy, p-methoxyphenoxy, etc., group), an amino group (e.g., a diethylamino, piperidino, morpholino, etc., group), an imino group, an acylamino group (e.g., an acetamido, etc., group), etc., and these substituents can, in turn, be additionally substituted. Suitable examples of aliphatic groups for $R_3$ include the following groups: isopropyl, isobutyl, tert-butyl, isoamyl, tert-amyl, 1,1-dimethylbutyl, 1,1-dimethylhexyl, 1,1-diethylhexyl, dodecyl, hexadecyl, octadecyl, cyclohexyl, 2-methoxyisopropyl, 2-phenoxyisopropyl, 2-p-tert-butylphenoxyisopropyl, α-(diethylamino)isopropyl, α-(succinimido)isopropyl, α-(phthalimido)isopropyl, α-(benzenesulfonamido)isopropyl, etc.

When $R_3$ or $R_4$ represents an aromatic group, particularly a phenyl group, the aromatic ring can be unsubstituted or substituted. The aromatic group such as a phenyl group can be substituted with one or more groups having 22 total carbon atoms or less, for example, an alkyl group (e.g., a methyl, ethyl, t-butyl, etc., group), an alkoxy group (e.g., a methoxy, ethoxy, tetradecyloxy, etc., group), an alkoxycarbonyl group (e.g., a methoxycarbonyl, ethoxycarbonyl, hexadecyloxycarbonyl, tetradecyloxycarbonylmethoxycarbonyl, etc., group), an alkoxycarbonylamino group (e.g., an ethoxycarbonylamino, dodecyloxycarbonylamino, etc., group), an aliphatic amino group (e.g., an acetamido, butanamido, hexanamido, hexadecanamido, etc., group), an alkylsulfamoyl group (e.g., an N,N-diethylsulfamoyl, N-tetradecylsulfamoyl, N-ethyl-N-hexylsulfamoyl, etc., group), an alkylsulfonamido group (e.g., a methylsulfonamido, hexadecanesulfonamido, etc., group), an alkylureido group (e.g., a 3-methylureido, 3-hexadecylureido, 3-octadecylureido, 3-cyclohexylureido, etc., group), an alkyl-substituted succinimido group (e.g., a dodecylsuccinimido, hexadecylsuccinimido, etc., group), etc. Further, the alkyl group can contain a divalent aromatic group such as a phenylene group in the chain thereof. The phenyl group as the aromatic group can also be substituted with one or more of an aryloxy group (e.g., a phenoxy, p-methoxyphenoxy, 2,4-di-tert-amylphenoxy, 3-pentadecylphenoxy, 4-tert-butylphenoxy, etc., group), an arylamido group (e.g., a benzamido, etc., group), an arylsulfamoyl group (e.g., an N-phenylsulfamoyl, N-ethyl-N-phenylsulfamoyl, etc., group), an arylsulfonamido group (e.g., a toluenesulfonamido, etc., group), an arylureido group (e.g., a 3-phenylureido, 3-p-chlorophenylureido, etc., group), etc. The aryl moiety of these substituents can be further substituted with one or more of an alkyl group (e.g., a methyl, tert-butyl, pentadecyl, etc., group), wherein the total number of carbon atoms contained is 1 to 22.

Furthermore, the aromatic group such as the phenyl group represented by $R_3$ or $R_4$ can be substituted with an amino group including an amino group substituted with a lower alkyl group of 1 to 6 carbon atoms (such as a methyl group, an ethyl group, an isopropyl group and the like), a hydroxy group, a carboxy group, a sulfo group, a nitro group, a cyano group or a halogen atom (e.g., a fluorine, chlorine, bromine, etc., atom).

Moreover, $R_3$ or $R_4$ can represent a substituent wherein a phenyl group is condensed with another ring, for example, to form a naphthyl group, a quinolyl group, an isoquinolyl group, a chromanyl group, a cumaranyl group, tetrahydronaphthyl group, etc. These groups can, in turn, have further substituents.

When $R_3$ or $R_4$ represents a heterocyclic group, the heterocyclic group is connected through a carbon atom which forms part of the heterocyclic ring to the carbon atom of the carbonyl group of the acyl group or the nitrogen atom of the amido group in the α-acylacetamido moiety. Examples of such heterocyclic rings having as hetero atoms one or more of oxygen, sulfur and nitrogen atoms include thiophene, furan, pyran, pyrrole, pyrazole, pyridine, pyrazine, pyrimidine, pyridazine, indolizine, imidazole, thiazole, oxazole, triazine, oxazine, etc. These heterocyclic groups can be unsubstituted or substituted with one or more substituents on the ring, e.g., as described for the aromatic group for $R_3$ or $R_4$.

In the general formula (IV), $R_5$ represents an aliphatic group having 1 to 32 carbon atoms, preferably 1 to 22 carbon atoms, including a straight chain or branched chain alkyl group (for example, a methyl, isopropyl, tert-butyl, hexyl, dodecyl, etc., group), an alkenyl group (for example, an allyl, etc., group), a cycloalkyl group (for example, a cyclopentyl, cyclohexyl, norbornyl, etc., group), an aralkyl group (for example, a benzyl, β-phenylethyl, etc., group), or a cycloalkenyl group (for example, a cyclopentenyl, cyclohexenyl, etc., group). These groups can be substituted with one or more of a halogen atom and a nitro, cyano, aryl, alkoxy, aryloxy, carboxy, alkylthiocarbonyl, arylthiocarbonyl, alkoxycarbonyl, sulfo, sulfamoyl, carbamoyl, acylamino, diacylamino, ureido, urethane, thiourethane, sulfonamido, heterocyclic, arylsulfonyl, alkylsulfonyl, arylthio, alkylthio, alkylamino, dialkylamino, anilino, hydroxy or mercapto group.

Further, $R_5$ represents an aryl group having up to 32 carbon atoms (for example, a phenyl, α- or β-naphthyl, etc., group). The aryl group can be unsubstituted or have one or more substituents. Examples of such substituents are, for example, a halogen atom and an alkyl, alkenyl, cycloalkyl, aralkyl, cycloalkenyl, nitro, cyano, aryl, alkoxy, aryloxy, carboxy, alkoxycarbonyl, sulfo, sulfamoyl, carbamoyl, acylamino, diacylamino, ureido, urethane, sulfonamido, heterocyclic, arylsulfonyl, alkylsulfonyl, arylthio, alkylthio, alkylamino, dialkylamino, hydroxy or mercapto group. Specific examples of these substituents include those described above for $R_1$ and $R_3$ or $R_4$. A phenyl group in which at least one of the orthopositions is substituted with an alkyl group, an alkoxy group or a halogen atom is preferred, since when the coupler remains in a color photographic material after development, less coloration due to the action of light or heat occur.

Furthermore, $R_5$ has up to 32, preferably up to 22, carbon atoms and represents a heterocyclic group (for example, a 5-membered or 6-membered heterocyclic group or a condensed heterocyclic group containing one or more of a nitrogen atom, an oxygen atom or a sulfur atom, as a hetero atom, such as a pyridyl, quinolyl, furyl, benzothiazolyl, oxazolyl, imidazolyl, naphthoxazolyl, etc., group), a heterocyclic group substituted with one or more of the substituents above-described for the aryl group for $R_5$, an aliphatic or aromatic acyl, alkylsulfonyl, arylsulfonyl, alkylcarbamoyl, arylcarbamoyl, alkylthiocarbamoyl or arylthiocarbamoyl group.

In the formula, $R_6$ represents a hydrogen atom or an aliphatic group having 1 to 32 carbon atoms, preferably 1 to 22 carbon atoms, including a straight chain or branched chain alkyl group, an alkenyl group, a cycloalkyl group, an aralkyl group and a cycloalkenyl group (in which examples of these groups are as described above for $R_5$ and in which these groups can be substituted with one or more of the substituents above-described for $R_5$), an alkoxy group (for example, a methoxy, ethoxy, heptadecyloxy, etc., group), an acylamino group (for example, an acetamido, 3-[(2,4-di-tert-amylphenoxy)acetamido]benzamido, etc., group), an N-alkylacylamino group (for example, an N-methylpropionamido, etc., group), a ureido group (for example, a ureido, N-arylureido, N-alkylureido, etc., group), a urethane group, an arylamino group (for example, a phenylamino, N-methylanilino, N-acetylanilino, 2-chloro-5-tetradecanamidoanilino, 2-chloro-5-N-tetradecylsulfamoylanilino, 2,4-dichloro-5-hexadecylanilino, etc., group), an alkylamino group (for example, an n-butylamino, methylamino, cyclohexylamino, etc., group), a cycloamino group (for example, a piperidino, pyrrolidino, etc., group), a heterocyclic amino group (for example, a 4-pyridylamino, 2-benzoxazolylamino, etc., group) or a sulfonamido group (for example, an alkylsulfonamido, arylsulfonamido, etc., group).

In the formula, $R_7$ represents a hydrogen atom or an aliphatic group having 1 to 32 carbon atoms, preferably 1 to 22 carbon atoms, including a straight chain or branched chain alkyl group, an alkenyl group, a cycloalkyl group, an aralkyl group, and a cycloalkenyl group (e.g., as exemplified above for $R_5$) and these groups can be substituted with one or more of the substituents above-described for $R_5$.

Further, $R_7$ represents an aryl group or a heterocyclic group, e.g., as exemplified above for $R_5$, and these groups can be substituted with one or more of the substituents above-described for $R_5$.

Furthermore, $R_7$ represents a halogen atom or a cyano, alkoxy, aryloxy, carboxy, alkoxycarbonyl, sulfo, sulfamoyl, carbamoyl, acylamino, diacylamino, ureido, urethane, sulfonamido, arylsulfonyl, alkylsulfonyl, arylthio, alkylthio, alkylamino, dialkylamino, hydroxy or mercapto group. Specific examples of these substituents include those described above for $R_3$ or $R_4$.

In the formula, $R_8$, $R_{11}$ and $R_{14}$ each represents an aliphatic group having 1 to 32 carbon atoms, preferably 1 to 22 carbon atoms, including a straight chain or branched chain alkyl group (for example, a methyl, ethyl, ethylthiomethyl, octadecyl, etc., group), an alkoxy group (for example, a methoxy, tetradecyloxy, etc., group), an alkylthio group (for example, a methylthio, butylthio, hexadecylthio, etc., group), an acylamino group (for example, an acetamido, tetradecanamido, 2-(2,4-di-tert-amylphenoxy)butanamido, perfluorobutanamido, etc., group), a diacylamino group, a ureido group (for example, an N-phenylureido, N-dodecylureido, etc., group), a urethane group (for example, an ethoxycarbonylamino, tetradecyloxycarbonylamino, etc., group) or a sulfonamido group (for example, a methanesulfonamido, p-toluenesulfonamido, hexadecanesulfonamido, etc., group).

$R_9$ and $R_{10}$ each represents a hydrogen atom, a halogen atom (for example, a fluorine, chlorine, etc., atom), an alkyl group having 1 to 10 carbon atoms, preferably 1 to 5 carbon atoms (for example, a methyl, butyl, t-butyl, etc., group) or an alkoxy group having 1 to 10 carbon atoms, preferably 1 to 5 carbon atoms (for example, a methoxy, butoxy, etc., group).

$R_{12}$ and $R_{13}$ each represents a hydrogen atom, an aliphatic group including an alkyl group having 1 to 32, preferably 1 to 20 carbon atoms (for example, a methyl, ethyl, butyl, hexadecyl, etc., group) and a substituted alkyl group (for example, a 2-cyanoethyl, 2-chloroethyl, 3-(2,4-di-tert-butylphenoxy)propyl, 2-dodecyloxyethyl, etc., group) or an aryl group including an unsubstituted aryl group (for example, a phenyl, naphthyl, etc., group) and an aryl group having one or two substituents. Suitable examples of substituents include a halogen atom (for example, a fluorine, chlorine, etc., atom) or a group having 1 to 22 carbon atoms, preferably 1 to 18 carbon atoms, including an alkyl, alkoxy, alkoxycarbonyl, carbamoyl, sulfamoyl, acylamino, sulfonamido, succinimido, etc., group.

The coupler used in the present invention can provide various properties depending on the $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ substituents and this feature is applicable to various photographic objects. When at least one of $R_3$ to $R_{14}$ above-described contains a ballast group of 8 or more carbon atoms, preferably 12 or more carbon atoms, the coupler becomes non-diffusible in the hydrophilic colloid layer of a light-sensitive material. Such a coupler can be incorporated into a silver halide emulsion layer. When $R_1$ or $R_2$ contains a ballast group and $R_3$, $R_4$, $R_5$, $R_6$, $R_7$, $R_8$, $R_9$, $R_{10}$, $R_{11}$, $R_{12}$, $R_{13}$ and $R_{14}$ do not contain a diffusion resistant group and at least one of $R_3$, $R_4$, $R_5$, $R_6$, $R_7$, $R_8$, $R_9$, $R_{10}$, $R_{11}$, $R_{12}$, $R_{13}$ and $R_{14}$ contains a water-solubilizing group such as a sulfo group or a carboxy group, the coupler per se is non-diffusible but can provide a diffusible dye by the oxidizing coupling reaction with an aromatic primary amine developing agent. Such a diffusible dye providing coupler is suitable for use in diffusion transfer color photography.

A diffusible coupler is used by being dissolved in a developer solution and provided in an emulsion layer through diffusion during development to form a color image.

A diffusion resistant coupler is used by adding such to an emulsion layer. In order to render a coupler diffusion resistant, a ballast group containing a hydrophobic residue of 8 to 40 carbon atoms is introduced into the coupler molecule by combining such a group with the coupler skeleton directly or through an imino bond, an ether bond, a thioether bond, a carbonamido bond, a sulfonamido bond, a ureido bond, an ester bond, a carbonyl bond, an imido bond, a carbamoyl bond, a sulfamoyl bond, etc.

Examples of suitable ballast groups are an alkyl group, an alkoxyalkyl group, an alkenyl group, an aryl group substituted with an alkyl group, an aryl group substituted with an alkoxy group, a terphenyl group and the like. These ballast groups can be substituted with one or more of a halogen atom such as fluorine, chlorine, etc., a nitro group, an amino group, a cyano group, an alkoxycarbonyl group, an aryloxycarbonyl group, an amido group, a carbamoyl group, a sulfamoyl group, a ureido group, a sulfonamido group and the like.

Specific examples of suitable ballast groups are 2-ethylhexyl, tert-octyl, n-dodecyl, 2,2-dimethyldodecyl, n-octadecyl, 2-(n-hexyl)decyl, 9,10-dichloroctadecyl, 2,4-di-tert-amylcyclohexyl, dodecyloxypropyl, oleyl, 2,4-di-tert-amylphenyl, 2,4-di-tert-amyl-6-chlorophenyl, 3-n-pentadecylphenyl, 2-dodecyloxyphenyl, 3-hexadecyloxyphenyl, o-terphenyl, perfluoroheptyl and the like.

Further, some specific examples of ballast groups are shown in the specific examples of the couplers of the present invention given hereinafter.

Typical examples of the couplers according to the present invention are illustrated below, but the present invention is not to be construed as being limited to only these couplers.

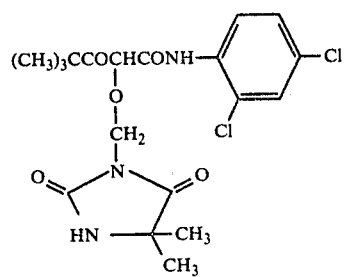
(1)
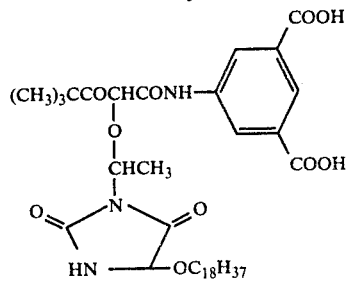
(2)
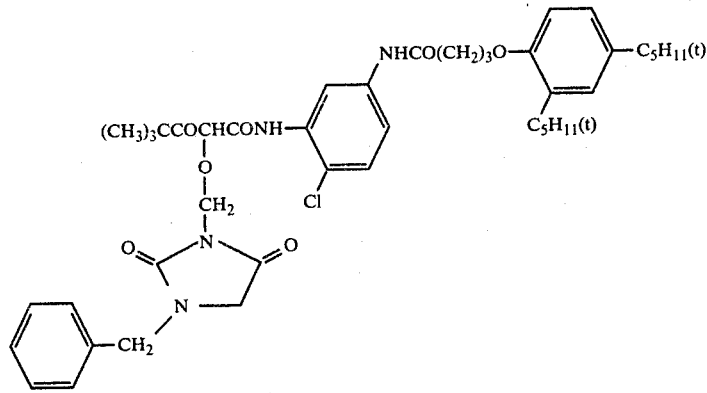
(3)
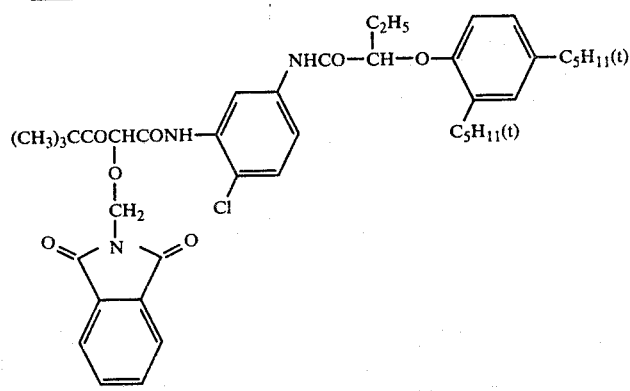
(4)
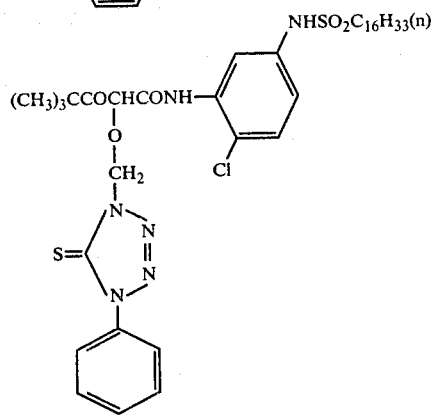
(5)

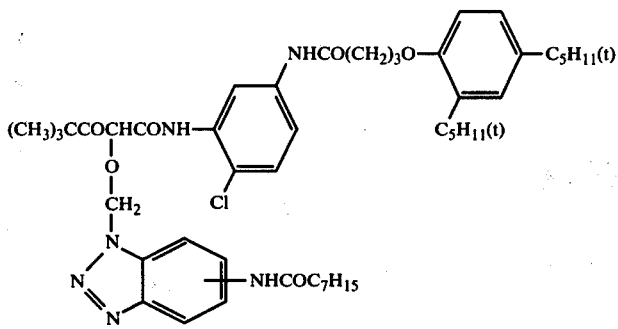
(6)
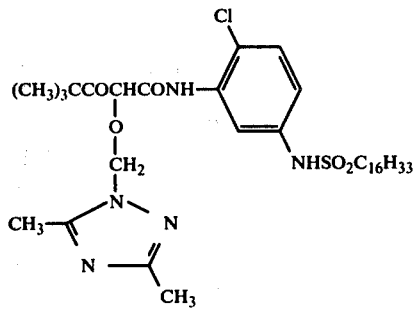
(7)
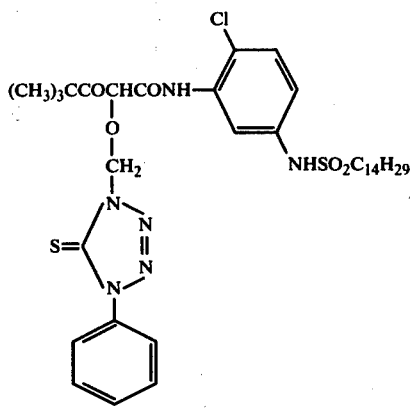
(8)
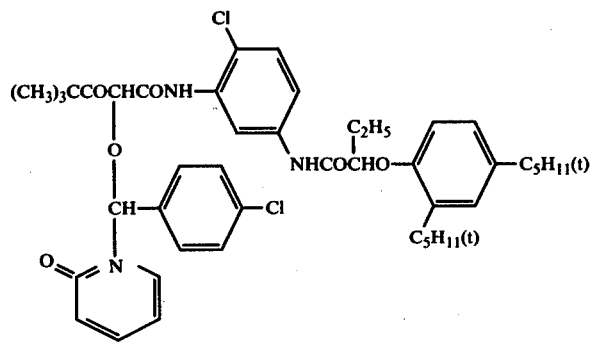
(9)
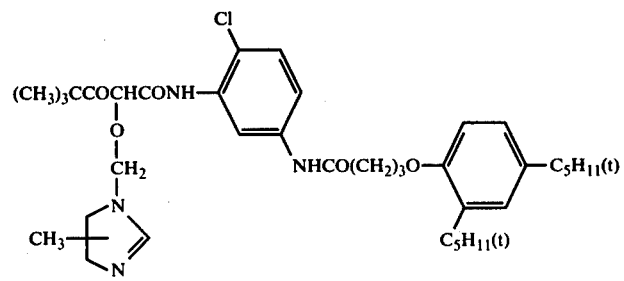
(10)

(11)
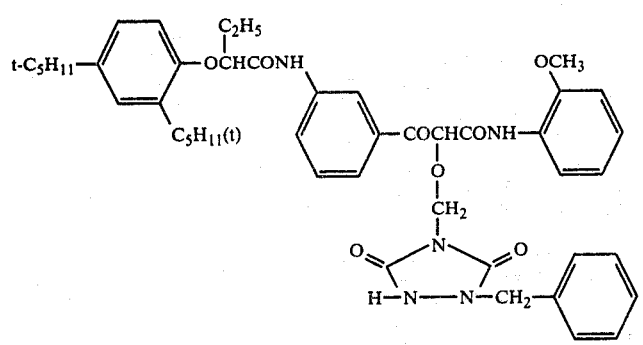
(12)
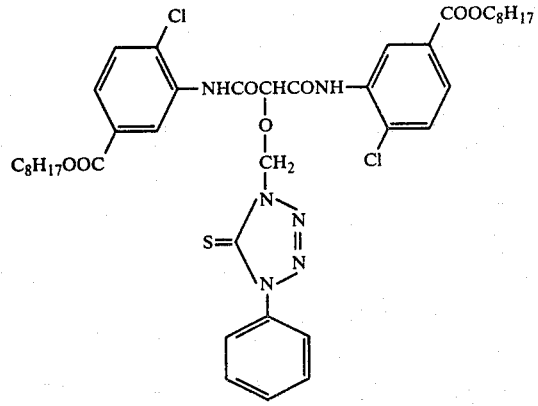
(13)
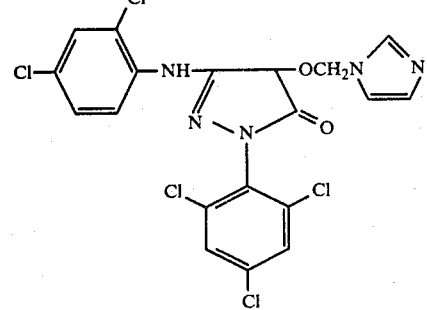
(14)
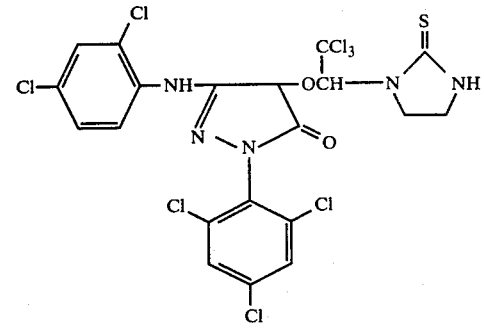
(15)
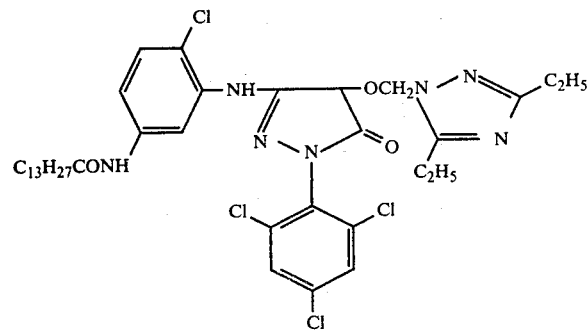

-continued
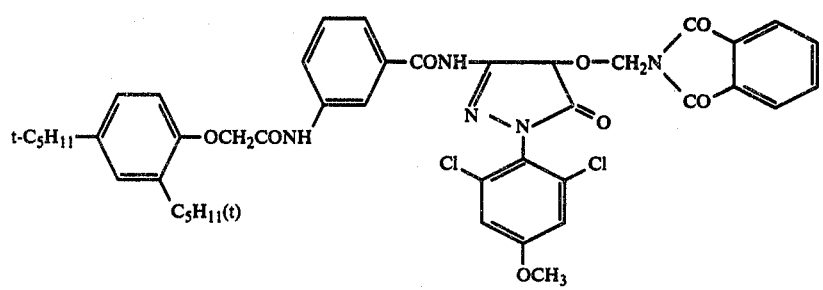 (16)
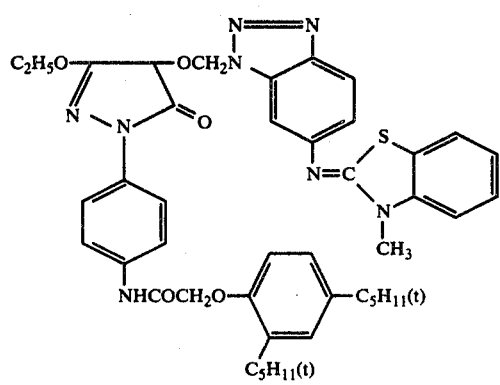 (17)
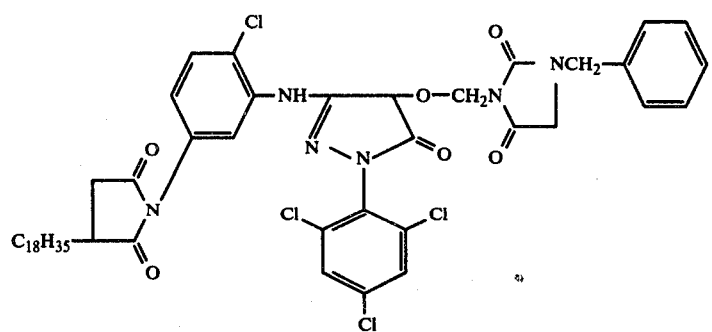 (18)
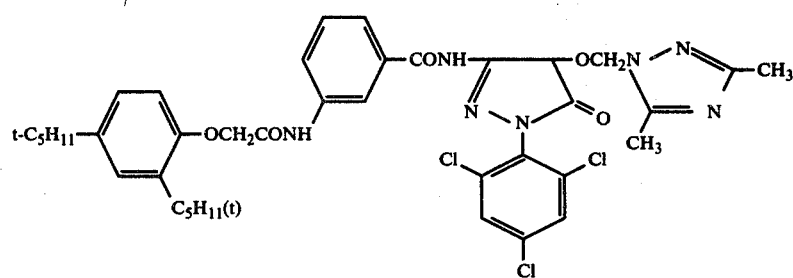 (19)
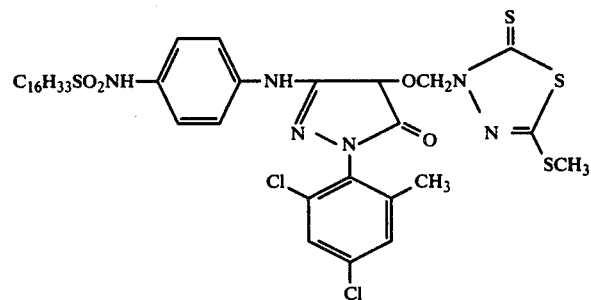 (20)

-continued
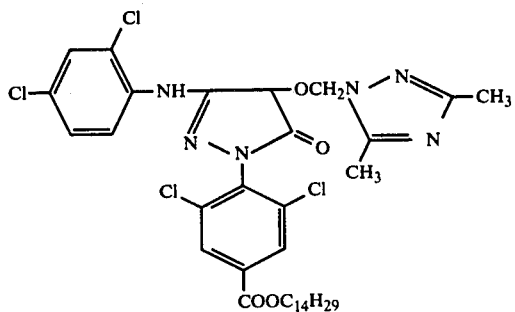
(21)
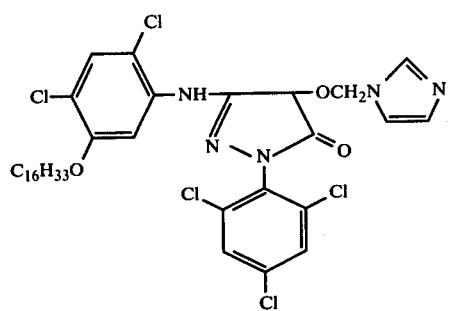
(22)
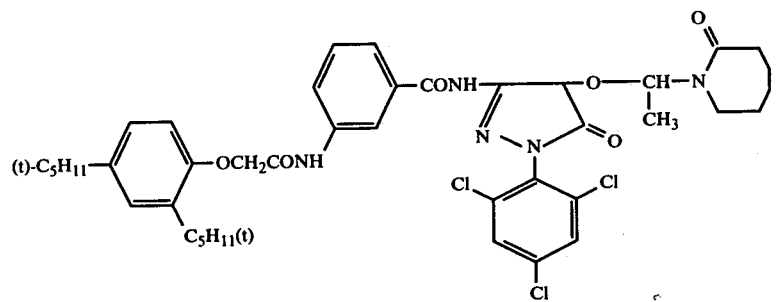
(23)
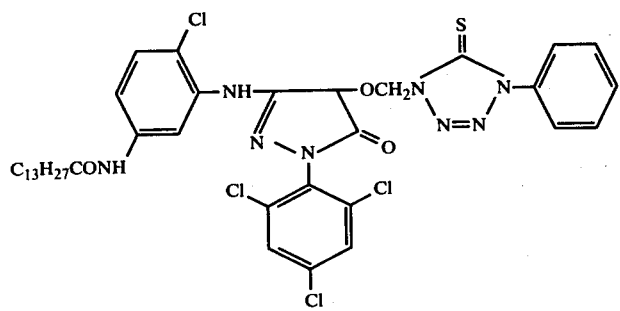
(24)
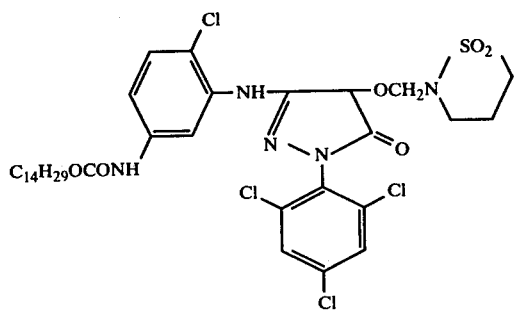
(25)

-continued
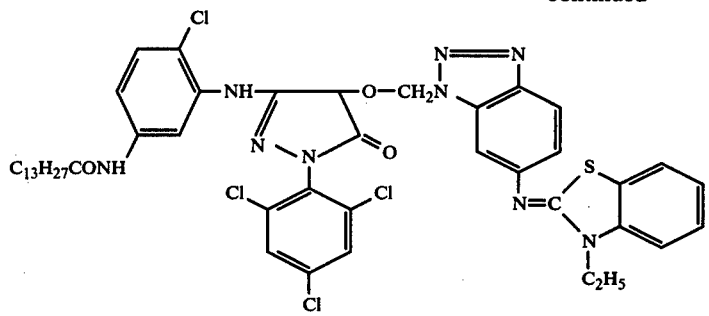 (26)
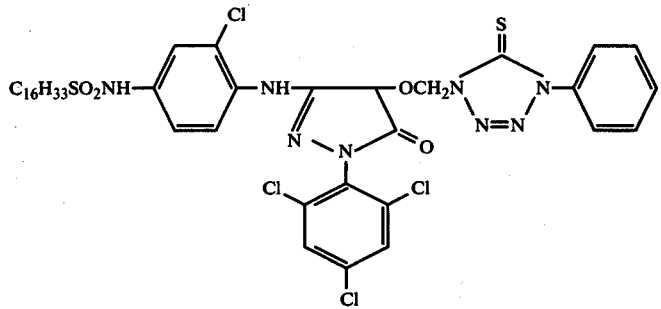 (27)
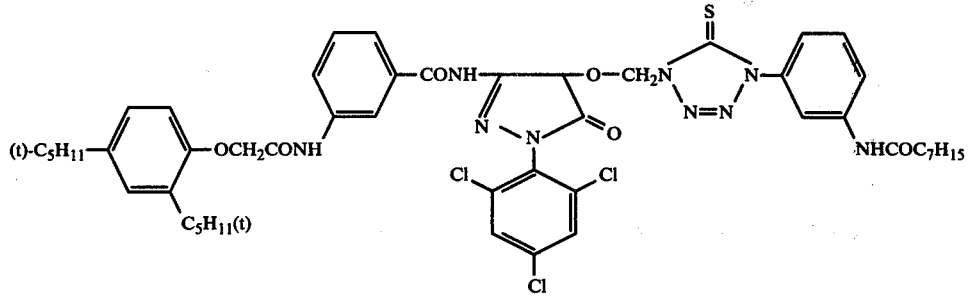 (28)
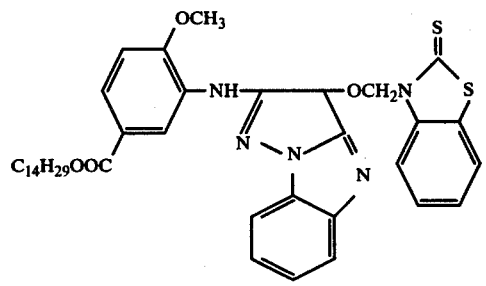 (29)
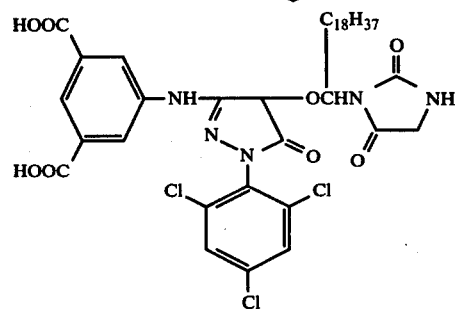 (30)
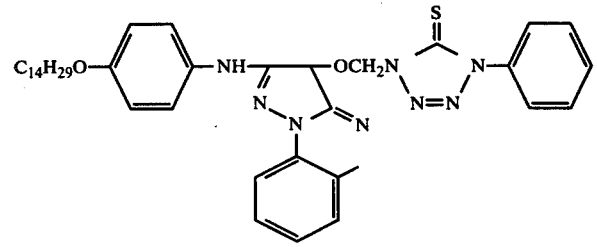 (31)

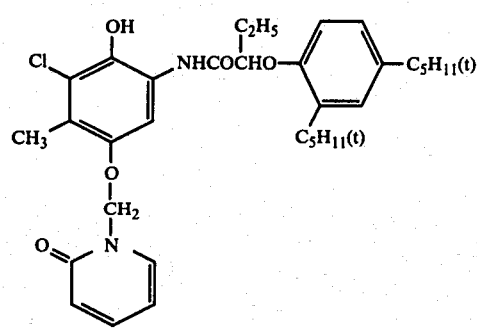 (32)
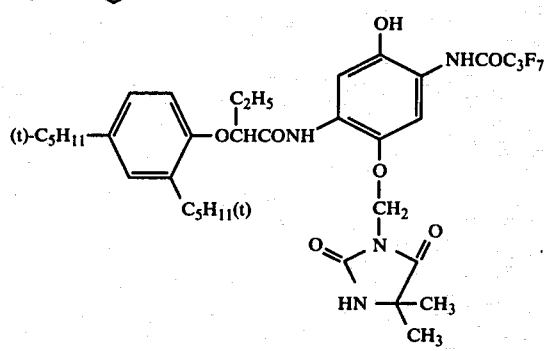 (33)
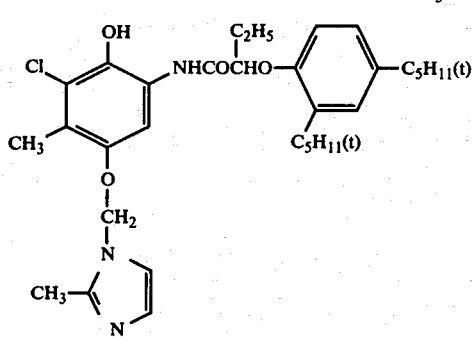 (34)
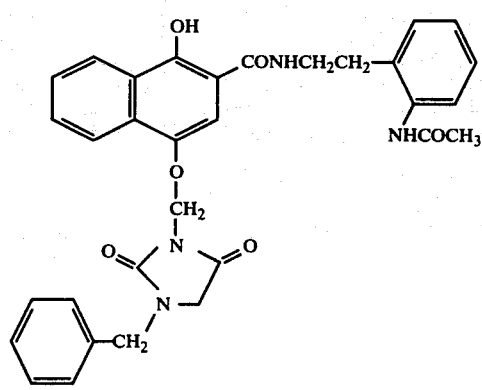 (35)
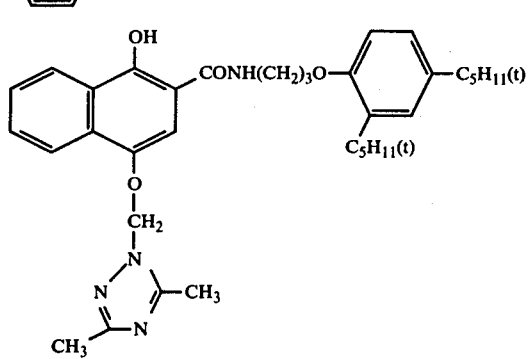 (36)

-continued
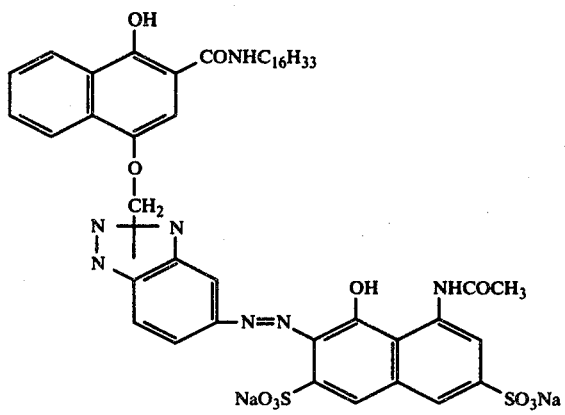 (37)
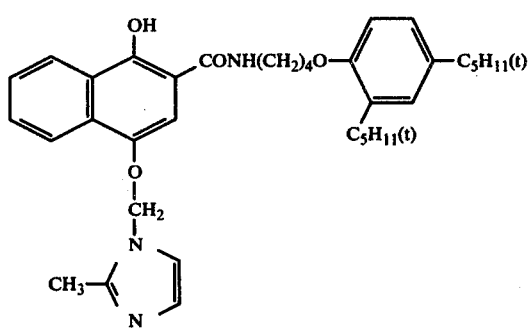 (38)
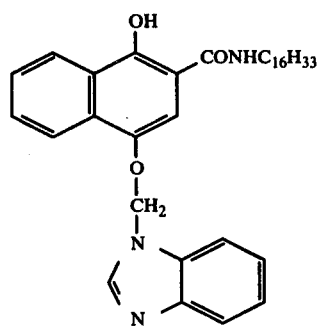 (39)
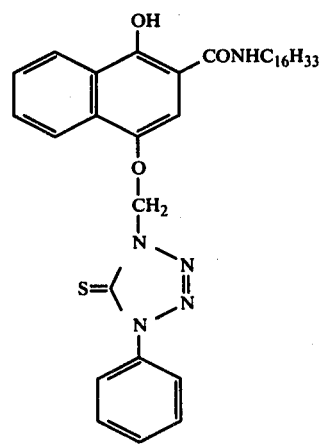 (40)

(41)
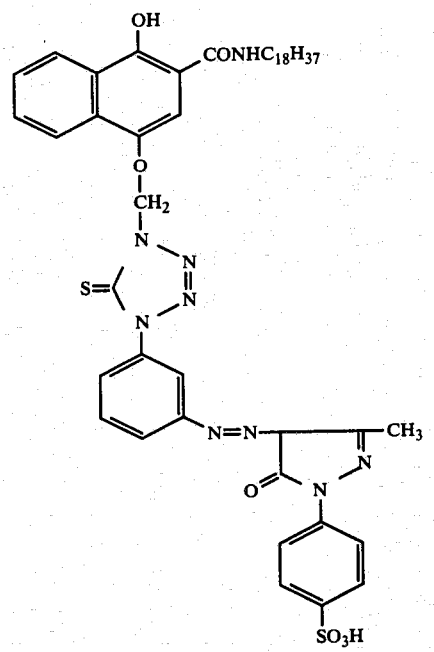
(42)
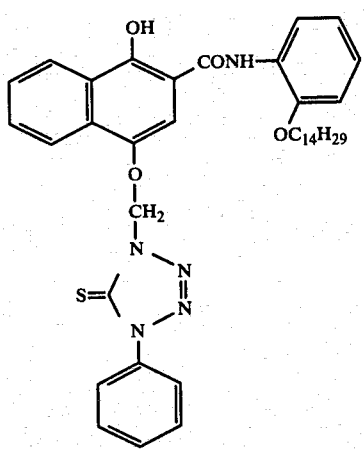
(43)
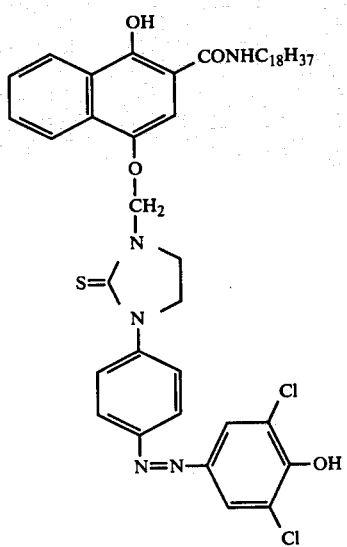

-continued
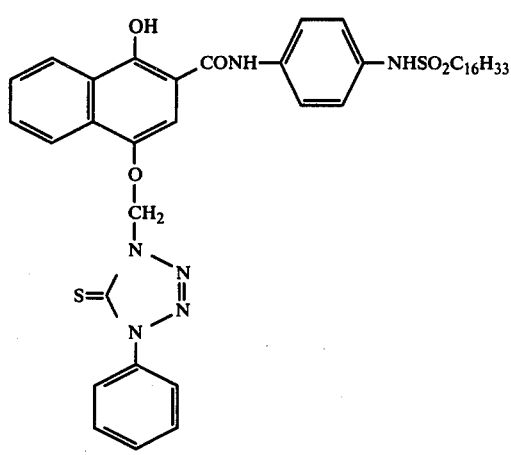
(44)
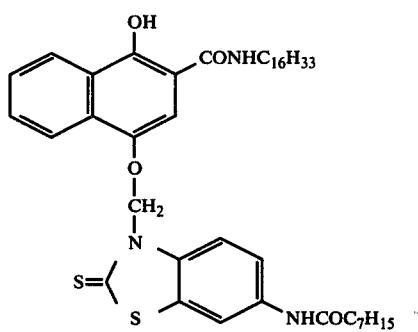
(45)
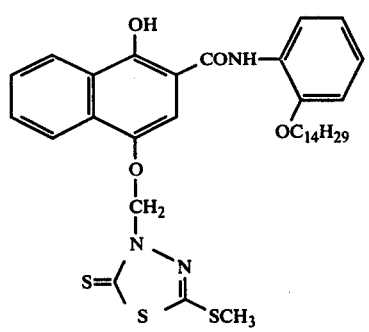
(46)
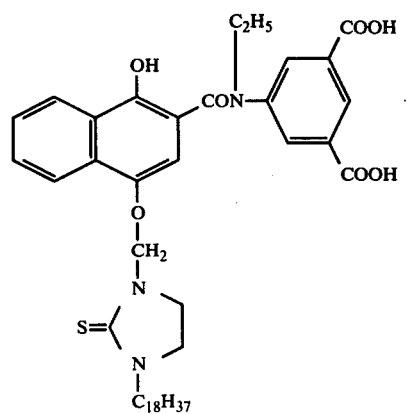
(47)

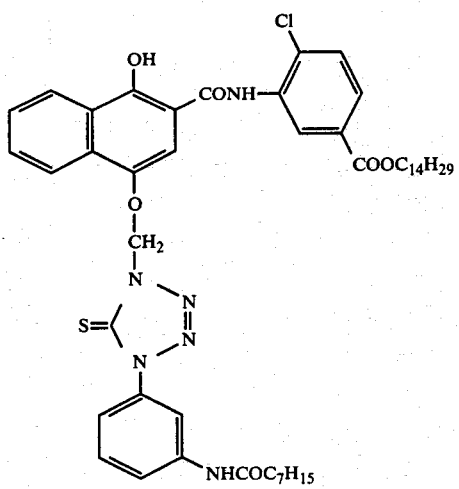
(48)
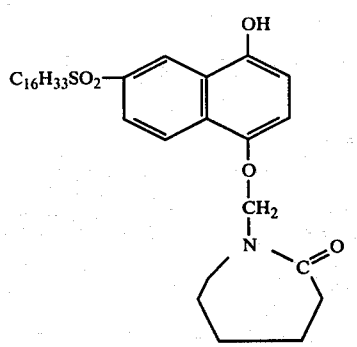
(49)
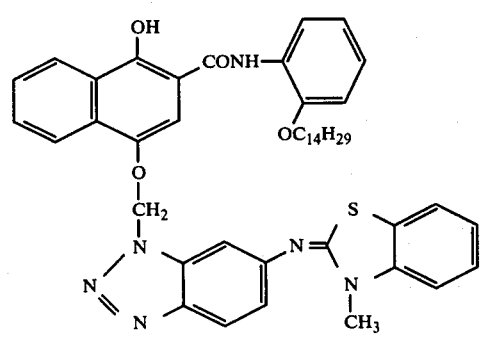
(50)
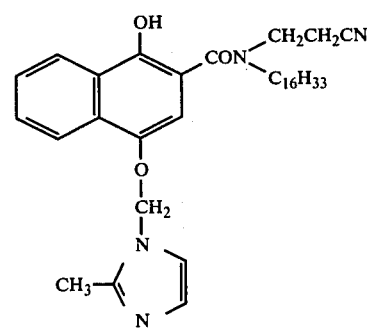
(51)

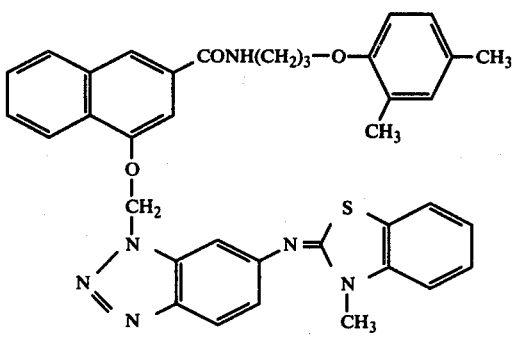

(52)

The coupler, in which a releasable group is bonded through an oxygen atom of the couplers according to the present invention can be generally prepared by replacing a hydrogen atom at the coupling position of a four equivalent mother coupler by a hydroxy group and then reacting it with a corresponding α-substituted alkyl halide. The α-substituted alkyl halide is generally prepared as shown in the following reaction schematic:

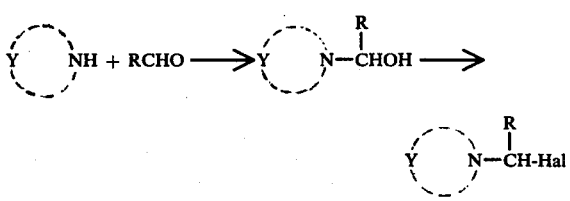

wherein R and Y each has the same meaning as hereinbefore defined.

More specifically, hydroxymethyl compounds or their α-substituted derivatives can be obtained by reacting cyclic amines and aldehydes in the absence of a solvent or in the presence of a solvent such as water, acetic acid, methanol, ethanol, propanol, ethyl acetate, acetonitrile, ethyl ether, tetrahydrofuran, benzene, toluene, xylene, etc., in amounts of about 1 to 20 times by volume the amount of both reactants at a temperature of from room temperature (e.g., 20°–25° C.) to about 140° C., preferably from 40° C. to 140° C., for a time of from about 20 minutes to about 3 hours, preferably from 30 minutes to 8 hours. The molar ratio of the aldehydes to the cyclic amines preferably ranges from about 1:1 to about 1.5:1. The thus obtained hydroxymethyl compounds or their derivatives and thionyl chloride or phosphorous oxychloride with a suitable molar ratio of reactants being about 1:1.2 to 1:1.5 are reacted with stirring in the absence of a solvent or in the presence of a solvent such as benzene, toluene, etc., in an amount about 3 to about 20 times by volume the amounts of both reactants at room temperature or about 40° C. to about 100° C. for about 1 to about 5 hours in order to produce the α-substituted alkyl chlorides.

In this reaction, the corresponding α-substituted alkyl bromides can be obtained by substituting thionyl bromide for thionyl chloride or by substituting phosphorous oxybromide for phosphorous oxychloride.

As a method for introducing a hydroxy group into the coupling position, the method of Ramiretz et al., (*J. Am. Chem. Soc.*, Vol. 92, page 6939, (1970)) or the method as described in U.S. Pat. No. 3,408,194 can be used in the case of an open chain ketomethylene coupler. The methods as described in U.S. Pat. Nos. 3,311,476 and 3,419,391 can be used in the case of a 5-oxo-2-pyrazoline coupler or a pyrazolo-[1,5-a]-benzimidazole coupler. Further, the method as described in U.S. Pat. No. 3,311,476 can be used in the case of a phenol coupler or a naphthol coupler.

Typical synthesis examples of the couplers according to the present invention are illustrated below. Unless otherwise indicated herein, all parts, percents, ratios and the like are by weight.

SYNTHESIS EXAMPLE 1

Preparation of
α-Pivaloyl-α-(5,5-dimethyl-3-hydantoinyl)-methoxy-2,4-dichloroacetanilide [Coupler (1)]

5,5-Dimethylhydantoin was heated at 70° to 80° C. for 3 hours in an aqueous formaldehyde solution to prepare 5,5-dimethyl-3-hydroxymethylhydantoin and then it was reacted with thionyl chloride to prepare 5,5-dimethyl-3-chloromethylhydantoin. α-Pivaloyl-α-hydroxy-2,4-dichloroacetanilide prepared by the method of Ramiretz et al., was dissolved in dimethylformamide (DMF) together with 1.5 times on a molar basis of sodium ethoxide and a DMF solution of an equimolar amount of 5,5-dimethyl-3-chloromethylhydantoin was added thereto at room temperature (about 20°–25° C.) with stirring. After stirring for 2 hours at 40° to 50° C., the mixture was poured into water and the precipitates formed were collected by filtration, dried and recrystallized from ethanol to obtain Coupler (1).

SYNTHESIS EXAMPLE 2

Preparation of
α-Pivaloyl-α-(1-benzyl-3-hydantoinyl)methoxy-2-chloro-5-[γ-(2,4-di-tert-amylphenoxy)-butyramido]acetanilide [Coupler (3)]

α-Pivaloyl-α-(1-benzyl-3-hydantoinyl)methoxy-2-chloro-5-nitroacetanilide was prepared in the same manner as described in Synthesis Example 1 and it was reduced by hydrogenation using a Raney nickel catalyst in an ethanol solution to α-pivaloyl-α-(1-benzyl-3-hydantoinyl)methoxy-2-chloro-5-amino acetanilide. This was reacted with γ-(2,4-di-tert-amylphenoxy)butanoyl chloride in acetonitrile in the presence of triethylamine to obtain Coupler (3).

SYNTHESIS EXAMPLE 3

Preparation of 1-(2,4,6-Trichlorophenyl)-3-(2,4-dichloroanilino)-4-(1-imidazolyl)methoxy-5-oxo-2-pyrazoline [Coupler (13)]

1-Hydroxymethylimidazole which was prepared by reacting imidazole and formaldehyde was reacted with thionyl chloride to prepare 1-chloromethylimidazole. This was reacted with an equimolar amount of 1-(2,4,6-trichlorophenyl)-3-(2,4-dichloroanilino)-3-hydroxy-5-oxo-2-pyrazoline in DMF in the presence of 1 to 3 times on a molar basis of sodium ethoxide to obtain Coupler (13).

SYNTHESIS EXAMPLE 4

Preparation of 2-Chloro-3-methyl-4-(1-α-pyridonyl)methoxy-6-[α-(2,4-di-tert-amylphenoxy)butyramido]phenol [Coupler (32)]

2-Methyl-3-chloro-4-(tetrahydropyran-2-yloxy)-5-[α-(2,4-di-tert-amylphenoxy)butyramidophenol was reacted with 1 to 1.5 times on a molar basis of 1-chloromethyl-α-pyridone in DMF in the presence of 1 to 3 times mol of sodium ethoxide. After completion of the reaction, the mixture was poured into water and the precipitates formed were collected by filtration. The precipitates were dissolved in ethanol and dilute hydrochloric acid (5%) was added thereto. After stirring for 30 minutes at 50° C., the solution was poured into water. The precipitates formed were collected by filtration and recrystallized from acetonitrile to obtain Coupler (32).

SYNTHESIS EXAMPLE 5

Preparation of 1-Hydroxy-4-(3,5-dimethyl-1,2,4-triazol-1-yl)-methoxy-N-[γ-(2,4-di-tert-amylphenoxy)propyl]-2-naphthamide [Coupler (36)]

1-Hydroxymethyl-3,5-dimethyl-1,2,4-triazole which was prepared from 3,5-dimethyl-1,2,4-triazole and formaldehyde was reacted with 1.5 to 5 times on a molar basis of thionyl chloride to prepare 1-chloromethyl-3,5-dimethyl-1,2,4-triazole. This was reacted with an equimolar amount of 1,4-dihydroxy-N-[γ-(2,4-di-tert-amylphenoxy)propyl]-2-naphthamide in DMF in the presence of 1.5 to 3 times on a molar basis of sodium ethoxide to obtain Coupler (36).

SYNTHESIS EXAMPLE 6

Preparation of 1-Hydroxy-4-(1-phenyl-2-tetrazolin-5-thione-4-yl)methoxy-N-(2-tetradecyloxy)phenol [Coupler (42)]

1-Phenyl-4-hydroxymethyltetrazolin-5-thione which was prepared from 1-phenyl-5-mercaptotetrazole and an excess amount of formaldehyde was reacted with 2 to 5 times on a molar basis of thionyl chloride in benzene at 50° C. for 3 hours to prepare 1-phenyl-4-chloromethyltetrazolin-5-thione. This was reacted with an equimolar amount of 1,4-dihydroxy-N-(2-tetradecyloxy)-phenylnaphthamide in DMF in the presence of 1.5 to 3 times on a molar basis of sodium ethoxide to obtain Coupler (42).

SYNTHESIS EXAMPLE 7

Preparation of 1-Hydroxy-4-[6-(3-methyl-2-benzothiazolinylidene)-amino-1-benzotriazolyl]methoxy-N-(2-tetradecyloxy)-phenylnaphthamide [Coupler (50)]

By repeating the procedures of Synthesis Example 6 but using 1-chloromethyl-6-[N-methylbenzothiazolimino]benzotriazole hydrochloride in place of 1-phenyl-4-chloromethyltetrazolin-5-thione, Coupler (50) was obtained.

In order to produce silver halide photographic light-sensitive materials, the couplers of the present invention can be used individually or two or more of the couplers can be used as a mixture.

In the color photographic light-sensitive materials containing the couplers of the present invention, other couplers, for example, a DIR coupler other than that of the present invention or a DIR compound (for example, those described in U.S. Pat. Nos. 3,632,345, 3,227,554 and 3,379,529, Japanese Pat. Application (OPI) Nos. 122,335/1974, 34,232/1975 and 135,310/1975, etc.), a yellow dye forming coupler (for example, those described in German Patent Application (OLS) No. 2,213,461, U.S. Pat. Nos. 3,510,306, 3,644,498 and 3,894,875, etc.), a magenta dye forming coupler (for example, those described in U.S. Pat. No. 3,615,506, German Patent Applications (OLS) Nos. 2,418,959 and 2,424,467, etc.) and a cyan dye forming coupler (for example, those described in U.S. Pat. Nos. 2,474,293, 3,034,892, 3,591,383 3,311,476 and 3,476,563, etc.) can be incorporated.

The silver halide emulsions which can be used in the present invention include silver chloride and silver bromide and also mixed silver halides such as silver chlorobromide, silver iodobromide, silver chloroiodobromide, etc.

The silver halide emulsion can be produced according to known methods (for example, a single or double jet method, a controlled double jet method, etc.).

Furthermore, silver halide grains wherein latent images are formed in the surface portion thereof or those wherein latent images are formed in the interior portion thereof can be used.

The silver halide emulsion is preferably sensitized with a known chemical sensitizer, for example, sodium thiosulfate, N,N,N'-trimethyl thiourea, aurous thiocyanate complex salt, aurous thiosulfate complex salt, stannous chloride, hexamethylenetetramine, etc.

The silver halide grains can have fogged nuclei formed with a reducing agent such as hydrazine or a combination of a reducing agent and a gold compound or a labile sulfur compound.

The photographic emulsion used in the color photographic light-sensitive material containing the coupler according to the present invention can be spectrally sensitized to be sensitive to blue, green or red light using a cyanine dye such as a monomethinecyanine, pentamethinecyanine, merocyanine or carbocyanine dye, individually or in combination, or using a combination of these dyes and a styryl dye and aminostilbene compound or the like, if desired.

A known stabilizing agent or anti-fogging agent, for example, 4-hydroxy-6-methyl-1,3,3a,7-tetraazaindene, 3-methylbenzothiazole, 1-phenyl-5-mercaptotetrazole, another mercapto compound, a metal salt, etc., can be used in the photographic emulsion.

The formation of dye images with the coupler of the present invention can be achieved with various kinds of color photographic systems. One process comprises processing an image-wise exposed silver halide light-sensitive material with a color developer solution containing an aromatic primary amine color developing agent in which a coupler is dissolved to form a water-insoluble or diffusion resistant dye image in the emulsion layer, that is a coupler-in-developer type color process. Another process comprises processing an image-wise exposed light-sensitive material having a silver halide emulsion layer containing a diffusion resistant coupler with a color developer solution containing an aromatic primary amine color developing agent to form a water-insoluble or diffusion resistant dye image in the emulsion layer, that is a coupler-in-emulsion type color process. Still another process comprises processing an image-wise exposed light-sensitive photographic material having a silver halide emulsion layer in combination with a diffusion resistant coupler with an alkaline developer solution containing an aromatic primary amine color developing agent to form a diffusible dye which diffuses into an image receiving layer containing a hydrophilic colloid, that is, a diffusion transfer process.

Of the couplers of the present invention, for example, Couplers (1), (13), (14) and (35) can be used in the first process, Couplers (2), (30) and (47) can be used with the third process and the other couplers specifically illustrated hereinbefore can be used in the second process. Colored couplers such as Couplers (37), (41) and (43) can be used as a coupler for masking in order to compensate for undesirable absorption of a color image or as a diffusible dye releasing coupler which releases upon an oxidation coupling reaction with an aromatic primary amine a diffusible dye which forms a dye image in an image receiving layer. Further, of the illustrated couplers, Couplers (5), (6), (8), (12), (17), (20), (21), (22), (24), (26), (27), (28), (29), (31), (40), (42), (44), (45), (46) and (48) can release upon an oxidation coupling with an aromatic primary amine a group which changes to a development inhibiting compound. Therefore, these couplers achieve effects such as reduced graininess of the image, control of gradation, improvement of color reproduction, etc. Also, these couplers can be used in a diffusion transfer process in which effects of couplers on adjacent layers are employed.

The couplers of the present invention can be dispersed in the photographic emulsion after dissolving the couplers in an aqueous medium or an organic solvent.

Of the couplers of the present invention, oil-soluble diffusion resistant couplers which are suitable for use in a coupler-in-emulsion type system are advantageously dispersed in a photographic emulsion as a solution in an organic solvent. Specific examples of the process for dispersing the coupler are described in detail in U.S. Pat. No. 3,676,131. Suitable organic solvents for dissolving the coupler are those which are slightly soluble in water and have a high boiling point (e.g., about 140° C. or higher, preferably 180° C. or higher) and including, for example, a substituted hydrocarbon, a carboxylic acid ester, a benzoic acid ester, a citric acid ester, a carboxylic acid amide, a phosphoric acid ester and an ether. Specific examples of such solvents are di-n-butylphthalate, n-octylbenzoate, O-acetyltributylcitrate, tricresylphosphate, tri-n-hexylphosphate, N,N-diethylcaprylamide, and the like. In addition to these high boiling point solvents, it is advantageous to use an auxiliary solvent of a low boiling point (e.g., ranging from about 50° to 200° C., preferably from 55° to 180° C.) in order to assist the dissolution of the couplers. Examples of such auxiliary solvents are propylene carbonate, ethyl acetate, butyl acetate, cyclohexanol, tetrahydrofuran, cyclohexanone, etc.

It is advantageous to use a surface active agent to aid in finely dispersing the solvents in a hydrophilic colloid used for the photographic emulsion. Diffusion resistant couplers having a carboxylic acid group or a sulfonic acid group together with a ballast group in the molecule are soluble in a neutral or weakly alkaline aqueous solution. The aqueous solution containing the coupler can be added to a photographic emulsion.

The coupler of this invention is generally used in an amount of about 10 to 1,500 g per mol of silver halide. However, the amount can be varied depending on the purpose of use (e.g., $2.5 \times 10^{-5}$ to 0.25 mol of DIR coupler per mol of silver halide and 0.005 to 0.5 mol of dye-image forming coupler per mol of silver halide).

The coupler of the present invention can be employed with various types of silver halide light-sensitive materials, for example, color negative films, color positive films, color reversal films, color papers, and other various color light-sensitive materials. In addition, the coupler can be employed with color direct positive light-sensitive materials, instant color light-sensitive materials such as those for a color diffusion transfer process, etc.

The coupler of the present invention can be used in a multilayer color light-sensitive materials with known multilayer structures, for example, those described in U.S. Pat. Nos. 3,726,681 and 3,516,831, British Pat. Nos. 818,687 and 923,045, a method described in Japanese Patent Application (OPI) No. 5,179/1975, and a method in which the coupler is used together with a DIR compound as described in German Patent Application (OLS) No. 2,322,165 and U.S. Pat. No. 3,703,375.

The light-sensitive material used in the present invention can contain a p-substituted phenol derivative, for example, a hydroquinone derivative in an emulsion layer thereof or an adjacent layer thereto. This is advantageous for increasing the stability of the color photographic images formed. Particularly preferred p-substituted phenol derivatives are those described in U.S. Pat. Nos. 2,360,290, 2,418,613, 2,675,314, 2,710,801, 2,728,659, 2,732,300, 2,735,765, 2,816,028, 3,457,079 and 3,069,262, Japanese Patent Publication No. 13,496/1968, U.S. Patent 2,735,576, Japanese Patent Application (OPI) No. 4,738/1972, U.S. Pat. Nos. 3,432,300, 3,573,050, 3,574,627 and 3,764,337.

The light-sensitive material containing the coupler of the present invention can contain an ultraviolet absorbing agent as described, for example, in U.S. Pat. Nos. 3,250,617 and 3,253,921 in an emulsion layer or an adjacent layer thereto so as to stabilize the images formed.

The support for the color light-sensitive material of the present invention can be a cellulose acetate film, a cellulose acetate butyrate film, a polystyrene film, a polyethylene terephthalate film, a laminate of these films, glass, paper, a paper coated or laminated with baryta or a polymer of an α-olefin having 2 to 10 carbon atoms, such as polyethylene, polypropylene, an ethylene-butene copolymer, etc.

The photographic light-sensitive material containing the coupler of the present invention can be usually subjected, after exposure, to a known processing method including basically a color development step, a bleaching step and a fixing step. Each step can be conducted separately or two or more steps can be carried out as one step using a processing solution which has the capability of accomplishing these steps. For instance, the use of a bleach-fixing solution is one example of a single step accomplishing multiple functions. If desired, the processing can include other steps such as a prehardening, a neutralization, a first development (black and white development), an image stabilizing, a water washing, etc.

The processing temperature used sometimes is below about 18° C. but often advantageously is above about 18° C. Particularly, suitable temperatures which can be used range from about 20° to about 60° C. For a rapid processing a range of about 35° to about 60° C. is suitable.

A color developer solution for use in this invention is an alkaline aqueous solution having a pH of about 8 or above and particularly 9 to 12 which contains a color developing agent.

Preferred examples of color developing agents which can be used are 4-amino-N,N-diethylaniline, 3-methyl-4-amino-N,N-diethylaniline, 4-amino-N-ethyl-N-$\beta$-hydroxyethylaniline, 3-methyl-4-amino-N-ethyl-N-$\beta$-hydroxyethylaniline, 4-amino-3-methyl-N-ethyl-N-$\beta$-methanesulfonamidoethylaniline, 4-amino-3-methyl-N-ethyl-N-$\beta$-methoxyethylaniline, etc. In addition, the compounds described in U.S. Pat. Nos. 2,193,015 and 2,592,364, Japanese Patent Application (OPI) No. 64,933/1973 and L.F.A. Mason, *Photographic Processing Chemistry*, pages 226 to 229, Focal Press, London (1966) are also used.

The light-sensitive material containing the coupler of the present invention can be subjected to a color development even in the presence of a competing coupler such as citrazinic acid, etc., without practical damage.

After the color development step, the light-sensitive material of the present invention is subjected to a bleaching in a conventional manner. The bleaching can be carried out separately or simultaneously with fixing. In the latter case, a fixing agent is added to a bleaching solution to make a bleach-fixing bath. Many compounds can be used as a bleaching agent. For example, a ferricyanide, a bichromate, a complex salt of a polyvalent metal cation such as iron (III), cobalt (III), etc., and an organic acid, for example, a metal complex salt of an aminopolycarboxylic acid such as ethylenediaminetetraacetic acid, nitrilotriacetic acid, diaminopropanoltetraacetic acid, etc., citric acid, tartaric acid, malic acid, etc., can be used. It is possible to add to this processing solution a bleaching accelerating agent as described in U.S. Pat. Nos. 3,040,520 and 3,421,966, Japanese Patent Publications Nos. 8,506/1970 and 8,836/1970, etc., and other various additives.

The coupler of the present invention can be used for light-sensitive materials having a low silver content wherein the amount of silver halide in the emulsion is from about one half to about one hundredth of that in conventional light-sensitive materials, e.g., in color papers, color negative films and color reversal films, the amount of silver halide generally conventionally coated is about 7 to 20 mg/m², about 50 to 100 mg/m² and about 30 to 80 mg/m², respectively. It is possible to obtain a satisfactory color image in such color light-sensitive materials having a low silver halide content by using an image forming process which comprises a color intensification using a peroxide, a cobalt complex salt or sodium chlorite, for example, as described in German Patent Application (OLS) 2,357,694, U.S. Pat. Nos. 3,674,490 and 3,761,265, German Patent Applications (OLS) 2,044,833, 2,056,539, 2,056,360, 2,226,770, Japanese Patent Applications (OPI) 9,728/1973 and 9,729/1973, etc.

Advantageous results are obtained according to the present invention, some of which are described below.

(1) The amount of silver required to provide a specific color image density can be reduced. Thus, this provides the ability to reduce the thickness of the light-sensitive layer containing the coupler and to improve the sharpness of the image.

(2) A reduction in the cost of production of the light-sensitive material is achieved by using a reduced amount of silver halide.

(3) The heat fastness of the color image formed is improved by using the coupler of the present invention.

(4) Magenta couplers which are more stable to the effects of chemical compounds such as formaldehyde or acetone are provided.

(5) Couplers having a high developing reactivity are provided.

(6) A color image having a lesser degree of fog and stain is obtained.

(7) A silver halide color photographic light-sensitive material having good stability under storage is obtained by using the coupler of the present invention.

(8) The conversion yield into a dye is improved by using the coupler of the present invention.

(9) A color image free from silver is obtained by using the coupler of the present invention.

The present invention will be further illustrated by reference to the following examples. However, the present invention is not to be construed as being limited to these examples.

EXAMPLE 1

A solution prepared by heating at 40° C. a mixture of 52.5 g of the above-described Coupler (3), 60 ml of di-n-butyl phthalate and 120 ml of ethyl acetate was added to 600 ml of an aqueous solution containing 60 g of gelatin and 3.0 g of sodium p-dodecylbenzene sulfonate and stirred. The mixture was then passed five times through a colloid mill. The couplers were finely dispersed together with the solvent.

All of the dispersion thus prepared was added to 1 kg of a photographic emulsion containing 70 g of gelatin and 57.1 g of silver iodobromide (iodide content: 5.0 mol%) and 13.0 ml of a 4% aqueous solution of 2-hydroxy-4,6-dichloro-s-triazine sodium salt was added thereto as a hardener. The pH of the mixture was adjusted to 6.5 and then the mixture was coated on a cellulose triacetate film in a dry thickness of 6.0$\mu$ to prepare a photographic light-sensitive material. This material was designated Sample A. The amount of the coupler was 21.6 $\times$ 10$^{-4}$ mol/m² and the coated amount of silver was 90.1 $\times$ 10$^{-2}$ g/m² in Sample A.

For comparison, a photographic light-sensitive material was prepared using the same procedure as described in the preparation of Sample A except for the use of 42.8 g of $\alpha$-pivaloyl-2-chloro-5-[$\gamma$-(2,4-di-tert-amylphenoxy)butyramido]-acetanilide (Coupler (a)) in place of Coupler (3), 45 ml of di-n-butyl phthalate and 90 ml of ethyl acetate, the use of 2 kg of a photographic emulsion which was the same as described above and the use of 20.5 ml of an aqueous solution of the hardener which was the same as described above. This material was designated Sample B. The amount of the coupler was 21.8 × 10⁻⁴ mol/m² and the coated amount of silver was 189.0 × 10⁻² g/m² in Sample B.

These samples were subjected to a stepwise exposure followed by processing in the following manner.

| Processing Step | Temperature | Time |
|---|---|---|
| | (°C.) | (min.) |
| 1. Color Development | 20 | 15 |
| 2. Water Washing | 18 | 1 |
| 3. First Mixing | 20 | 4 |
| 4. Water Washing | 18 | 3 |
| 5. Bleaching | 20 | 5 |
| 6. Water Washing | 18 | 3 |
| 7. Second Fixing | 20 | 3 |
| 8. Water Washing | 18 | 15 |

| Color Developer Solution A | |
|---|---|
| Sodium Sulfite (anhydrous) | 3.0 g |
| 4-Amino-3-methyl-N,N-diethylaniline Hydrochloride | 2.5 g |
| Sodium Carbonate (monohydrate) | 47.0 g |
| Potassium Bromide | 2.0 g |
| Water to make | 1,000 ml |
| Fixing Solution | |
| Sodium Thiosulfate (hexahydrate) | 80 g |
| Sodium Sulfite (anhydrous) | 5 g |
| Borax | 6 g |
| Glacial Acetic Acid | 4 ml |
| Potassium Alum | 7 g |
| Water to make | 1,000 ml |
| Bleaching Solution | |
| Potassium Ferricyanide | 100 g |
| Potassium Bromide | 5 g |
| Boric Acid | 10 g |
| Borax | 5 g |
| Water to make | 1,000 ml (pH 7.2) |

After the processing, the transmission optical density to blue light of these samples was measured, whereby the following photographic characteristics as shown in Table 1 were obtained. Clear color images were obtained having an absorption maximum of 450 mμ.

TABLE 1

| Sample | Coupler | Sensitivity* | Gamma | Maximum Density |
|---|---|---|---|---|
| | | (relative value) | | |
| A | (3) | 100 | 2.33 | 3.20 |
| B | Coupler (a) (for comparison) | 93 | 1.90 | 2.87 |

*Relative value for the amount of exposure required to provide a density of fog + 0.10.

The maximum densities to blue light with respect to Samples A and B are shown in Table 2, which were obtained upon processing for different periods of developing time.

TABLE 2

| Sample | Coupler | AgX/Coupler | Developing Time (min.) | | | |
|---|---|---|---|---|---|---|
| | | (molar ratio) | 5 | 10 | 15 | 20 |
| A | (3) | 4/1 | 2.34 | 3.08 | 3.20 | 3.25 |
| B | Coupler (a) (for comparison) | 8/1 | 1.87 | 2.54 | 2.86 | 2.92 |

These results show that the coupler used in the present invention provides higher sensitivity, gradation and color density, and provides sufficient color density in a shortened period of developing time resulting in a decrease in the overall processing time even when the amount of silver halide per mol of the coupler is reduced to ½, in comparison with the comparison coupler in which the active methylene group is unsubstituted such as Coupler (a). This is because the coupler of the present invention has a higher coupling reactivity than the coupler in which the active methylene group is unsubstituted.

EXAMPLE 2

When Coupler (4) and Coupler (7) were used respectively in place of Coupler (3) in Example 1, results similar to those of Example 1 were obtained.

EXAMPLE 3

Each of Samples A and B prepared in Example 1 was subjected to a sensitometric stepwise exposure and then processed in the following manner.

| Processing Step | Temperature | Time |
|---|---|---|
| | (°C.) | (min.) |
| 1. Color Development | 30 | 5 |
| 2. Stopping | " | 2 |
| 3. Water Washing | " | 2 |
| 4. Bleach-Fixing | " | 6 |
| 5. Water Washing | " | 5 |

| Color Developer Solution B | |
|---|---|
| Benzyl Alcohol | 12.0 ml |
| Diethylene Glycol | 3.5 ml |
| Sodium Hexametaphosphate | 2.0 g |
| Sodium Sulfite (anhydrous) | 2.0 g |
| Sodium Carbonate (monohydrate) | 27.5 g |
| Hydroxylamine Sulfate | 2.0 g |
| 4-Amino-3-methyl-N-ethyl-N-(β-methanesulfonamidoethyl)aniline Sesquisulfate (monohydrate) | 4.0 g |
| Potassium Bromide | 1.0 g |
| Water to make | 1,000 ml |
| Stopping Solution | |
| Sodium Thiosulfate | 10.0 g |
| Ammonium Thiosulfate (70% aq. soln.) | 30.0 ml |
| Sodium Acetate | 5.0 g |
| Acetic Acid | 30.0 ml |
| Potassium Alum | 15.0 g |
| Water to make | 1,000 ml |
| Bleach-Fixing Solution | |
| Ferric Sulfate | 20.0 g |
| Disodium Ethylenediaminetetraacetate (dihydrate) | 36.0 g |
| Sodium Carbonate monohydrate) | 17.0 g |
| Sodium Sulfite | 5.0 g |
| Ammonium Thiosulfate (70% aq. soln.) | 100.0 ml |
| Boric Acid | 5.0 g |
| Water to make | 1,000 ml |

After the processing, the optical density to blue light of these samples was measured and then the samples were immersed in a 1.5% aqueous solution of potassium ferricyanide for two minutes followed by washing with water for 10 minutes and drying. The optical density to blue light of these samples thus processed was again measured. The results shown in Table 3 were obtained.

TABLE 3

| | | Treatment with 1.5% Aqueous Potassium Ferricyanide Solution | | | |
|---|---|---|---|---|---|
| | | Before Treatment | | After Treatment | |
| Sample | Coupler | Gamma | Maximum Density | Gamma | Maximum Density |
| A | (3) | 2.28 | 3.01 | 2.31 | 3.01 |
| B | Coupler (a) (for comparison) | 1.48 | 2.12 | 1.85 | 2.64 |

Further, the maximum transmission densities to near infrared light of Samples A and B which were obtained upon processing for different periods of bleach-fixing time were measured using a filter having a maximum absorption peak at 750 mμ. When silver remains in the film, an absorption density due to the silver is obtained by the above-described measurement. These results are shown in Table 4 below.

TABLE 4

| Sample | Coupler | Bleach-Fixing Time (min.) and Density of the Remaining Silver | | | |
|---|---|---|---|---|---|
| | | 3 | 4.5 | 6 | 8 |
| A | (3) | 0.05 | 0.04 | 0.03 | 0.03 |
| B | Coupler (a) (for comparison) | 0.28 | 0.20 | 0.11 | 0.05 |

As can be seen from the results in Table 3, with the coupler used in the present invention, the process of forming dye images is completed during the color development step and the bleach-fixing step. On the contrary with Coupler (a) in which the active methylene group is unsubstituted, the formation of the dye image in only about 80% completed and the remainder of the reaction products still exist in an uncolored form. In order to completely convert the uncolored compounds to dyes, a post-treatment with a strong oxidizing agent such as an aqueous solution of potassium ferricyanide is necessary.

Also, the results in Table 4 show that with the coupler of the present invention, developed silver formed upon color development is easily and rapidly removed with a bleach-fixing solution containing a weak oxidizing agent and a silver complex salt forming agent and thus color images of excellent color reproduction and transparency are obtained.

EXAMPLE 4

A mixture of 23.6 g of the above-described Coupler (16), 24 ml of dioctyl butyl phosphate and 60 ml of ethyl acetate was heated at 60° C. and the resulting solution was added to 250 ml of an aqueous solution of 60° C. containing 25 g of gelatin and 0.75 g of sodium dodecylbenzenesulfonate, followed by vigorous mechanical stirring using a homogenizer, thus obtaining a coupler dispersion. The resulting coupler dispersion was mixed with 200 g of a photographic emulsion containing 11.2 $\times 10^{-2}$ mol of silver chlorobromide (silver bromide 45 mol%, silver chloride 55 mol%) and 20 g of gelatin and after 10 ml of a 3% acetone solution of triethylenephosphamide as a hardener was added thereto, the final pH was adjusted to 6.5. The mixture was coated onto a cellulose triacetate film support in a dry thickness of 4.5µ (Sample C). This film contained, per m², 1.56 $\times 10^{-3}$ mol of the coupler and 6.3 $\times 10^{-3}$ mol of silver chlorobromide.

For comparison, 18.8 g of 1-(2,4,6-trichlorophenyl)-3-{3-[2,4-di-tert-pentylphenoxy)acetamido]benzamido}-5-oxo-2-pyrazoline (Coupler (b)) as a corresponding comparison coupler in which the coupling position was not substituted was dispersed, in place of the above-described coupler in a manner analogous to the above-described coupler, mixed with 400 g of the same emulsion as described above and coated onto a cellulose triacetate film support in a dry thickness of 5.1µ (Sample D). This film contained, per m², 1.57 $\times 10^{-3}$ mol of the coupler and 12.7 $\times 10^{-3}$ mol of silver chlorobromide.

These films were subjected to stepwise exposure and then to the following processing:

| Color Processing Step | Temperature (° C.) | Time |
|---|---|---|

-continued

| Color Processing Step | (° C.) | Time |
|---|---|---|
| 1. Color Development | 21 | 12 min |
| 2. Water Washing | " | 30 sec |
| 3. First Fixing | " | 4 min |
| 4. Water Washing | " | 4 min |
| 5. Bleaching | " | 8 min |
| 6. Water Washing | " | 4 min |
| 7. Second Fixing | " | 4 min |
| 8. Water Washing | " | 6 min |

| Color Developer Solution | |
|---|---|
| Sodium Hexametaphosphate | 2 g |
| Sodium Sulfite (anhydrous) | 2 g |
| Benzyl Alcohol | 5 ml |
| Sodium Carbonate (monohydrate) | 27.5 g |
| Potassium Bromide | 0.5 g |
| Hydroxylamine Sulfate | 2.5 g |
| N-Ethyl-N-(β-methanesulfonamidoethyl)-3-methyl-4-aminoaniline Sesquisulfate | 2.5 g |
| Water to make | 1,000 ml (pH 10.7) |

The fixing solution and the bleaching solution were the same as those used in Example 1, respectively.

After the processings, the optical density to green light of these films was measured to obtain the photographic properties as shown in Table 5 below. A clear color image was obtained having an absorption maximum of 542 mµ.

TABLE 5

| Sample | Gamma | Relative Sensitivity | Maximum Color Density |
|---|---|---|---|
| C | 2.59 | 100 | 3.08 |
| D (for comparison) | 2.17 | 97 | 2.41 |

The measurement of the relative sensitivity was the same as that in Example 1.

As is evident from the results in Table 5, the coupler of the present invention provided a higher sensitivity and gradation as well as a maximum color density in comparison with Coupler (b), even when the ratio of silver halide/coupler decreases to about ½. The above results demonstrate that in using the coupler of the present invention, the quantity of developed silver necessary for obtaining a color image having a specific density can be reduced. That is, the quantities of the coupler and coated silver halide necessary for obtaining a certain maximum color density can be reduced and thus the developing time for obtaining images having the desired characteristics can be shortened.

EXAMPLE 5

When the above-described Coupler (19) and Coupler (23) were used respectively in place of Coupler (16) in Example 4, results similar to those of Example 4 were obtained.

EXAMPLE 6

Using Sample C and Sample D as described in Example 4, after exposure, the following processing was carried out:

| Color Processing Step | Temperature (° C.) | Time (min.) |
|---|---|---|
| 1. Color Development | 30 | 4 |
| 2. Blixing | " | 2 |
| 3. Water Washing | " | 2 |
| 4. Stabilizing Bath | " | 2 |

-continued

| Color Developer Solution | |
|---|---|
| Sodium Metaborate | 25 g |
| Sodium Sulfite | 2 g |
| Hydroxylamine (sulfate) | 2 g |
| Potassium Bromide | 0.5 g |
| 6-Nitrobenzimidazole (nitrate) | 0.02 g |
| Sodium Hydroxide | 4 g |
| Benzyl Alcohol | 15.8 ml |
| Diethylene Glycol | 20 ml |
| 4-(N-Ethyl-N-β-methanesulfonamidoethyl)-amino-2-methylaniline Sesquisulfate | 8 g |
| Water to make | 1,000 ml |
| | (pH 10.2) |
| Blixing Solution | |
| Ferric Ethylenediaminetetraacetate | 45 g |
| Ammonium Thiocyanate | 10 g |
| Sodium Sulfite | 10 g |
| Ammonium Thiosulfate (60% aq. soln.) | 100 ml |
| Sodium Ethylenediaminetetraacetate | 5 g |
| Water to make | 1,000 ml |
| | (pH 6.9) |
| Stabilizing Bath (a) | |
| Tartaric Acid | 10 g |
| Zinc Sulfate | 10 g |
| Sodium Metaborate | 20 g |
| Water to make | 1,000 ml |
| Stabilizing Bath (b) | |
| Tartaric Acid | 10 g |
| Zinc Sulfate | 10 g |
| Sodium Metaborate | 20 g |
| Formaldehyde (40% aq. soln.) | 10 ml |
| Water to make | 1,000 ml |

The photographic properties of the thus obtained samples are shown in Table 6 below.

Moreover, for the stabilizing bath, two kinds of stabilizing baths, i.e., Stabilizing Bath (a) which did not contain formaldehyde and Stabilizing Bath (b) containing 1% of a 40% aqueous solution of formaldehyde were prepared. The films were treated respecitvely with these stabilizing baths, allowed to stand at 80° C. for one week and the decreasing ratio of the density was measured based on the initial density. The results obtained are shown in Table 7 below.

TABLE 6

| | Photographic Property (Stabilizing Bath (a)) | |
|---|---|---|
| Sample | Gamma | Maximum Color Density |
| C | 2.68 | 3.08 |
| D (for comparison) | 2.11 | 2.39 |

TABLE 7

| | Fastness of Color Image (80° C., Standing for One Week) | | | |
|---|---|---|---|---|
| | Stabilizing | Decreasing Ratio to Initial Density (%) | | |
| Sample | Bath | 0.5 | 1.0 | 2.0 |
| C | a | 10 | 8 | 6 |
| | b | 9 | 7 | 6 |
| D (for comparison) | a | 50 | 32 | 10 |
| | b | 11 | 8 | 6 |

The results in Table 6 show that the use of Sample C according to the present invention results in a sufficient image density even though a strong oxidizing agent (potassium ferricyanide) is not used as in the processing of Example 4 and that Sample C has superior photographic properties to Sample D containing a four equivalent coupler. The results in Table 7 show that Sample C according to the present invention provides a sufficient heat fastness even though such was not subjected to a stabilizing bath treatment containing formaldehyde.

EXAMPLE 7

When the samples described in Example 5 were treated in the same manner as described in Example 6, similar results were obtained.

EXAMPLE 8

To 10.6 g of the above-described Coupler (32), 10 ml of di-n-butylphthalate and 20 ml of ethyl acetate were added and heated at 50° C. to dissolve. The solution was added to 100 ml of an aqueous solution containing 10 g of gelatin and 0.5 g of sodium p-dodecylbenzene sulfonate and the mixture was mechanically stirred using a high speed agitator for 20 minutes, thereby yielding a fine dispersion of the coupler together with the solvent.

61.7 g of the fine dispersion was added to 100 g of a photographic emulsion containing 0.03 mol of silver chlorobromide (containing 50 mol% bromide) and 8 g of gelatin, and followed by the addition of a hardener (sodium 2,4-dichloro-6-hydroxytriazine in an amount of 1.3 wt% based on the gelatin) and the adjustment of pH in a similar manner to Example 1. The mixture was coated on a transparent cellulose triacetate film base to prepare a photographic light-sensitive material. This material was designated Sample E. The coupler content of the Sample E was $1.89 \times 10^{-3}$ mol/m$^2$. The amount of silver halide coated was $7.25 \times 10^{-3}$ mol/m$^2$.

For comparison, a photographic light-sensitive material prepared using the same procedure as described for Sample E except that 10 g of 2,4-dichloro-3-methyl-6-[α-(2,4-di-tert-amylphenoxy)butyramido]phenol (Coupler (c)] was used in place of Coupler (32) and 55.7 g of the coupler dispersion was used. This material was designated Sample F. The coupler content of Sample F was $1.89 \times 10^{-3}$ mol/m$^2$ which was substantially equal to that of Sample E. The amount of silver halide coated was $7.25 \times 10^{-3}$ mol/m$^2$.

These photographic light-sensitive materials were subjected to a stepwise sensitometric exposure followed by processing in the same manner as described in Example 4.

After the processing, the optical density of Samples E and F to red light was measured to obtain the results shown in Table 8 below.

TABLE 8

| Film Sample | Sensitivity* (relative value) | Gamma | Maximum Density |
|---|---|---|---|
| E | 100 | 3.45 | 3.61 |
| F (for comparison) | 96 | 3.21 | 3.38 |

*Same manner as Example 1.

For Sample E and Sample F, the maximum density to red light which was obtained upon processing for different periods of developing time is shown in Table 9 below.

TABLE 9

| | Developing Time (min.) | | |
|---|---|---|---|
| Film Sample | 4 | 8 | 15 |
| E | 3.55 | 3.58 | 3.61 |
| F (for comparison) | 3.19 | 3.37 | 3.42 |

These results show that the coupler in which the active position is substituted with a group represented by the general formula:

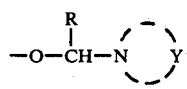

of the present invention provides higher sensitivity, gradation and color density, in comparison with a coupler in which the active position is substituted with a chlorine atom, such as Coupler (c), and also provides sufficient color density within a short period of time, consequently making it possible to shorten the processing time.

When the above-described Coupler (33) was used in place of the above-described Coupler (32) and the same procedure was repeated, high sensitivity, gradation and color density were again obtained. In this case, the superiorities of the coupler of the present invention to the coupler in which the active position was substituted with a chlorine atom was also demonstrated.

EXAMPLE 9

A mixture of 10.5 g of the above-described Coupler (51), 10 ml of tri-n-hexyl phosphate and 20 ml of ethyl acetate was heated at 50° C. to dissolve. The solution prepared was added to 100 ml of an aqueous solution containing 0.5 g of sodium p-dodecylbenzene sulfonate and 10 g of gelatin and the mixture was mechanically stirred vigorously, thereby yielding a fine dispersion of the coupler together with the solvent.

All of the coupler dispersion was added to 186 g of a silver iodobromide emulsion for a reversal film (containing 3 mol% iodide, $8.37 \times 10^{-2}$ mol of silver and 13.0 g of gelatin), and to which 12 ml of a 4% aqueous solution of 2-hydroxy-4,6-dichloro-s-triazine sodium salt was added as a hardener. The pH of the mixture was adjusted to 7.0 and then the mixture was coated on a polyethylene terephthalate film support in a coated silver amount of 0.90 g/m² ($1.85 \times 10^{-3}$ mol/m²).

The sample thus prepared was subjected to a stepwise sensitometric exposure followed by processing in the following manner.

| Processing Step | Temperature | Time |
|---|---|---|
| | (°C.) | (min.) |
| 1. First Development | 30 | 3 |
| 2. Washing | " | 0.5 |
| 3. Reversal Exposure | Uniform exposure of 8,000 lux . sec. to the emulsion surface | |
| 4. Second Development | 30 | 4 |
| 5. Washing | " | 1 |
| 6. Bleaching | " | 1 |
| 7. Washing | " | 0.5 |
| 8. Fixing | " | 1 |
| 9. Washing | " | 1 |

The compositions of the processing solutions used were as follows.

| First Developer Solution | |
|---|---|
| 4-(N-Methylamino)phenol Sulfate | 2 g |
| Sodium Sulfite | 90 g |
| Hydroquinone | 8 g |
| Sodium Carbonate (monohydrate) | 52.5 g |
| Potassium Bromide | 5 g |
| Potassium Thiocyanate | 1 g |
| Water to make | 1,000 ml |

Second Developer Solution

| -continued | |
|---|---|
| Benzyl Alcohol | 5 ml |
| Sodium Sulfite | 5 g |
| Hydroxylamine Hydrochloride | 2 g |
| 4-Amino-3-methyl-N-ethyl-N-(β-ethoxyethyl)aniline p-Toluenesulfonate | 3 g |
| Potassium Bromide | 1 g |
| Trisodium Phosphate | 30 g |
| Sodium Hydroxide | 0.5 g |
| Ethylenediamine (70% aq. soln.) | 7 ml |
| Water to make | 1,000 ml |

| Bleaching Solution | |
|---|---|
| Potassium Ferricyanide | 100 g |
| Sodium Acetate | 40 g |
| Sodium Sulfite | 20 g |
| Potassium Alum | 30 g |
| Water to make | 1,000 ml |

| Fixing Solution | |
|---|---|
| Sodium Thiosulfate | 150 g |
| Sodium Acetate | 70 g |
| Sodium Sulfite | 10 g |
| Potassium Alum | 20 g |
| Water to make | 1,000 ml |

The reversal color image thus obtained had an absorption maximum at 685 mμ and exhibited excellent color.

Further, another sample of the coated sample was stored at 40° C., 75% relative humidity, for 3 days and subjected to a stepwise sensitometric exposure and to the above-described processing. The results were compared with those obtained above and no substantial differences in photographic properties such as maximum density, fog, gamma, sensitivity, etc., were observed. It is clear that the coupler of the present invention has superior stability.

EXAMPLE 10

The following samples were prepared.

Sample 101

0.2 mol (92.4 g) of Cyan Coupler (j) was dissolved in a mixture of 100 ml of tricresyl phosphate and 200 ml of ethyl acetate. The solution was dispersed in 1 kg of a 10% aqueous gelatin solution using 4 g of sodium nonylbenzene sulfonate (surface active agent) to prepare Dispersion (I). 400 g of Dispersion (I) was added to 1 kg of a silver iodobromide emulsion (silver content: 0.6 mol, iodide content: 6 mol%) and stirred. To the mixture there was added as a hardener an aqueous solution of 2 g of sodium 2,4-dichloro-6-hydroxytriazine. The thus prepared coating solution was coated on a transparent cellulose triacetate film support at a silver coated amount of 1.5 g/m². On this layer, a solution prepared by adding 2 g of sodium 2,4-dichloro-6-hydroxytriazine to a 10% aqueous gelatin solution was coated at a dry thickness of 1.5μ to form a protective layer.

Samples 102 to 112

Samples 102 to 112 were prepared in the same manner as Sample 101 except that the coupler as shown in Table 10 below was used in place of Cyan Coupler (j) and the compound as shown in Table 10 was further added in the amount as shown in Table 10 to the solvent (dispersion medium) in which the coupler was dissolved.

The compounds used for the preparations of the above-described samples were:

Coupler (j): 1-Hydroxy-N-[γ-(2,4-di-tert-amylphenoxy)propyl]-2-naphthamide

Coupler (k): 1-(2,4,6-Trichlorophenyl)-3-[3-(2,4-di-tert-amylphenoxyacetamido)benzamido]-5-oxo-2-pyrazoline (four equivalent coupler)

Coupler (l): α-(1-Benzyl-5-ethoxy-3-hydantoinyl)-α-pivaloyl-2-chloro-5-(hexadecanesulfonamido)acetanilide Samples 101 to 112 were exposed stepwise using a white light source and then subjected to the following processing steps at 38° C.

| | |
|---|---|
| 1. Color Development | 3 min and 15 sec |
| 2. Bleaching | 6 min and 30 sec |
| 3. Washing | 3 min and 15 sec |
| 4. Fixing | 6 min and 30 sec |
| 5. Washing | 3 min and 15 sec |
| 6. Stabilizing | 3 min and 15 sec |

The processing solutions used in the above steps had the following compositions:

| Color Developer Solution | |
|---|---|
| Sodium Nitrilotriacetate | 1.0 g |
| Sodium Sulfite | 4.0 g |
| Sodium Carbonate | 30.0 g |
| Potassium Bromide | 1.4 g |
| Hydroxylamine Sulfate | 2.4 g |
| 4-(N-Ethyl-N-β-hydroxyethylamino)-2-methylaniline Sulfate | 4.5 g |
| Water to make | 1,000 ml |
| Bleaching Solution | |
| Ammonium Bromide | 160.0 g |
| Ammonia (28% aq. soln.) | 25.0 ml |
| Sodium Ferric Ethylenediamine-tetraacetate | 130 g |
| Glacial Acetic Acid | 14 ml |
| Water to make | 1,000 ml |
| Fixing Solution | |
| Sodium Tetrapolyphosphate | 2.0 g |
| Sodium Sulfite | 4.0 g |
| Ammonium Thiosulfate (70% aq. soln.) | 175.0 ml |
| Sodium Bisulfite | 4.6 g |
| Water to make | 1,000 ml |
| Stabilizing Solution | |
| Formaldehyde (35% by weight aq. soln.) | 8.0 ml |
| Water to make | 1,000 ml |

After the processing, the photographic characteristics (relative inertia speed: Si and gradation: γ) using blue, green and red light, respectively, of Samples 101 to 103, Samples 104 to 108 and Samples 109 to 112 were measured. The results obtained are shown in Table 10.

Further, these samples were line image exposed to soft X-rays through a slit with a 4 mm width and a slit with a 10 μ width and subjected to the same processing as above. After the processing, the optical density of these samples was measured by microdensitometer traces with the light source of the same color as described above. When a density of line image with a 10 μ width is designated $D_1$ of line image with a 4 mm width is designated $D_\infty$, the value of $(D_1-D_\infty)/D_1$ means an amount of edge effects of the sample. The value of $(D_1-D_\infty)/D_1$ of each sample is also shown in Table 10.

TABLE 10

| | | | | Photographic Property | | |
|---|---|---|---|---|---|---|
| | Primary Coupler | Compound Added | | | | Edge Effects |
| Sample | (Image Forming Coupler) | Compound | Amount | Si | γ | $(D_1 - D\infty)/d_1$ |
| 101 | Yellow Coupler (j) | — | — | 100 | 1.36 | −0.02 |
| 102 | " | Compound (5) | 5 | 98 | 0.69 | 0.35 |
| 103 | " | (6) | 5 | 101 | 0.77 | 0.40 |
| 104 | Magenta Coupler (k) | — | — | 100 | 1.40 | −0.05 |
| 105 | " | Compound (22) | 5 | 98 | 0.58 | 0.52 |
| 106 | " | (26) | 5 | 97 | 0.62 | 0.59 |
| 107 | " | (27) | 5 | 97 | 0.55 | 0.40 |
| 108 | " | (31) | 5 | 101 | 0.91 | 0.35 |
| 109 | Cyan Coupler (l) | — | — | 100 | 1.34 | −0.02 |
| 110 | " | Compound (40) | 5 | 99 | 0.80 | 0.40 |
| 111 | " | (42) | 5 | 96 | 0.54 | 0.53 |
| 112 | " | (50) | 5 | 98 | 0.49 | 0.62 |

Amount*mol% to the amount of the primary coupler

It is apparent from these results that the samples containing the coupler of the present invention have extremely large effects on softening gradation without any substantial loss in sensitivity in comparison with Samples 101, 104 and 109 which do not contain such a compound. These effects are the so-called DIR effects and particularly useful for improving graininess, sharpness (due to edge effects) and color reproduction (due to interlayer effects). As shown in Table 10, the edge effects of the samples containing the coupler of the present invention are very large in comparison with the samples which do not contain such a compound.

Further, by optical microscopic observation of the magenta color image obtained through the above-described processing, it was found that the samples containing the coupler of the present invention show extremely fine graininess in comparison with the samples which do not contain such a compound.

EXAMPLE 11

The following samples were prepared.

Sample 201

On a transparent cellulose triacetate film support were coated the following first layer to fourth layer in this order and dried to prepare the sample. The composition and method for preparation of the coating solution which was used for each layer was as follows.

First Layer: Red-Sensitive Emulsion Layer 1 kg of a high speed silver iodobromide emulsion (silver content: 0.4 mol, iodide content: 6 mol%) was spectrally sensitized using $4 \times 10^{-5}$ mol of Sensitizing Dye (I) per mol of silver and $1 \times 10^{-5}$ of Sensitizing Dye (II) per mol of silver. 550 g of Dispersion (I) prepared by dissolving 100 g of Cyan Coupler (1) into 100 ml of tricresyl phosphate and 200 ml of ethyl acetate, and then dispersing the resulting solution into 1 kg of a 10% aqueous gelatin solution using 4 g of sodium nonylbenzene sulfonate was added to the spectrally sensitized silver iodobromide emulsion and stirred. To the mixture an aqueous solution of 2 g of sodium 2,4-dichloro-6-hydroxytriazine was added as a hardener. The thus prepared coating solution was coated on a transparent cellulose triacetate film support at a silver coated amount of 1.5 g/m².

Second Layer: Intermediate Layer 50 g of 2,5-di-tert-octylhydroquinone was dissolved in 100 ml of tricresyl phosphate and dispersed in 1 kg of a 10% aqueous gelatin solution in the same manner as described in Dispersion (I). 250 g of the thus prepared dispersion and an aqueous solution of 2 g of sodium 2,4-dichloro-6-hydroxytriazine were added to 1 kg of a 10% aqueous gelatin solution and stirred. The coating solution was coated at a dry thickness of 1.5 μ.

Third Layer: Green-Sensitive Emulsion Layer 1 kg of a high speed silver iodobromide emulsion (same as used in the First Layer) was spectrally sensitized using $3 \times 10^{-5}$ mol of Sensitizing Dye (III) per mol of silver and $1 \times 10^{-5}$ mol of Sensitizing Dye (IV) per mol of silver. Using 100 g of Magenta Coupler (k), Dispersion (II) was prepared in the same manner as described in Dispersion (I). 700 g of Dispersion (II) was added to the spectrally sensitized silver iodobromide emulsion and an aqueous solution of 2 g of sodium 2,4-dichloro-6-hydroxytriazine was added thereto with stirring.

Fourth Layer: Protective Layer

To 1 kg of a 10% aqueous gelatin solution was added 2 g of sodium 2,4-dichloro-6-hydroxytriazine. The solution was coated at a dry thickness of 1.5 μ.

Samples 202 to 205

Samples 202 to 205 were prepared in the same manner as Sample 201 except that the optimum amount of a DIR coupler (as shown in Table 11 below) was additionally incorporated into the oil of the coupler solvent in Dispersion (I) of Sample 201.

Sample 206

Sample 206 was prepared in the same manner as Sample 201 except that the coated amount of the coating solution for the First Layer was reduced by 30%.

The compounds used for the preparations of the above-described samples were as follows:

Sensitizing Dye (I): Pyridinium salt of anhydro-5,5'-dichloro-3,3-di-sulfopropyl-9-ethylthiacarbocyanine hydroxide Sensitizing Dye (II): Triethylamine salt of anhydro-9-ethyl-3,3'-di-(3-sulfopropyl)-4,5,4',5'-dibenzothiacarbocyanine hydroxide Sensitizing Dye (III): Sodium salt of anhydro-9-ethyl-5,5'-dichloro-3,3'-sulfopropyloxacarbocyanine Sensitizing Dye (IV): Sodium salt of anhydro-5,6,5,6-tetrachloro-1,1-diethyl-3,3-sulfopropoxyethoxyethylimidazolocarbocyanine hydroxide Coupler (o): 1-Hydroxy-4-(1'-phenyltetrazol-5'-ylthio)-N-[γ-(2,4-di-tert-amylphenoxy)propyl]-2-naphthamide Coupler (p): α-(4-octadecyloxybenzoyl)-α-(5- or 6-bromo-1-benzotriazolyl)-2-methoxyacetanilide Samples 201 to 206 were exposed stepwise using red light and then exposed uniformly using green light, and processed in the same manner as described in Example 10. In addition, these samples were line image exposed to soft X-rays through a slit with a 4 mm width and a slit with a 10 μ width and subjected to the same processing as above.

In the characteristic curve thus obtained, when the gradation of the curve of the red filter optical density vs log (exposure amount) (which corresponds to the First Layer) is designated γR and the gradation of the curve of the green filter optical density vs log (exposure amount) (which corresponds to the Third Layer) is designated γG, the value of γG/γR is considered to be the amount of interlayer effects (color correction effects) from the First Layer to the Third Layer (γR values of the samples other than Sample 201 are substantially constant). That is, the value of γG/γR is minus and the greater the numerical value is the larger are the interlayer effects. The γG/γR value of each sample is shown in Table 11 below.

The optical density of each sample by line image exposure with soft X-rays was measured by microdensitometer tracing with red light. When the density of the line image with a 10 μ width is designated $D_1^R$ and a density of line image with a 4 mm width is designated $D_\infty^R$ the value of $(D_1^R - D_\infty^R)$ means the amount of edge effects of the sample when the sample is observed with red light. The value of $(D_1^R - D_\infty^R)/D_1^R$ of each sample is shown in Table 11 below.

Furthermore, each sample was exposed stepwise with white light, processed in the same manner as described in Example 10 and the RMS graininess of the color image thereof was measured using green light. The results of RMS graininess at densities of 0.5 and 1.5 are shown in Table 11 below.

TABLE 11

| | | | Photographic Properties | | | | |
|---|---|---|---|---|---|---|---|
| | Compound Added | | | Inter-Layer Effects | Edge Effects | RMS Graininess | |
| Sample | Compound | Amount | γR | (γG/γR) | $(D_1^R = D_\infty^R)/D_1$ | $D_R = 0.5$ | $D_R = 1.5$ |
| 201 | — | — | 1.35 | 0.04 | −0.01 | 0.058 | 0.052 |
| 202 | Compound (42) | 2.5 | 0.73 | −0.31 | 0.46 | 0.036 | 0.033 |
| 203 | Compound (50) | 2.5 | 0.75 | −0.39 | 0.59 | 0.033 | 0.030 |
| 204 | Coupler (o) (for comparison) | 8 | 0.72 | −0.08 | 0.16 | 0.044 | 0.045 |
| 205 | Coupler (p) (for comparison) | 15 | 0.74 | −0.21 | 0.21 | 0.053 | 0.049 |

TABLE 11-continued

| Sample | Compound Added Compound | Amount | γR | Inter-Layer Effects (γG/γR) | Edge Effects $(D_1^R = D_\infty^R)/D_1$ | RMS Graininess $D_R = 0.5$ | $D_R = 1.5$ |
|---|---|---|---|---|---|---|---|
| 206 | — | — | 0.75 | 0.07 | −0.08 | 0.055 | 0.050 |

Note
[1] Amount: mol% to Coupler (j)
[2] The sensitivities of all samples were approximately equal.
[3] RMS Graininess: measured with a slit of 10 μ × 10 μ.

Smaller numerical values in Table 11 show better graininess.

The measurement of the graininess by the RMS method is well known in the photographic art and is described in D. Zwick & B. L. Brothers Jr., "RMS Granularity; Determination of Just-noticeable Difference" *Photographic Science and Engineering*, Vol. 19, No. 4, pp. 235 to 238 (1975).

EXAMPLE 12

The following samples were prepared.

Sample 301

The sample was prepared in the same manner as Sample 101 in Example 10 except that 0.2 mol (134 g) of Coupler (k) and 0.15 mol (12.3 g) of the above-described Coupler (26) are used in place of 0.2 mol (92.4 g) of Coupler (j).

Samples 302 to 304

Samples 302 to 304 were prepared in the same manner as Sample 301 except that the above-described Coupler (27), Coupler (q) and Coupler (r) were used in place of the above-described Coupler (26), respectively.

The compounds used for the preparations of these samples were:

measured and the characteristics obtained are shown in Table 12 below.

TABLE 12

| | | Room Temperature (for 4 days) | | 45° C., 80% RH (for 4 days) | |
|---|---|---|---|---|---|
| Sample | Compound Added | Relative Sensitivity | Gamma | Relative Sensitivity | Gamma |
| 301 | Compound (26) | 98 | 0.63 | 95 | 0.62 |
| 302 | Compound (27) | 99 | 0.59 | 97 | 0.57 |
| 303 | Coupler (q) (for comparison) | 97 | 0.69 | 58 | 0.41 |
| 304 | Coupler (r) (for comparison) | 96 | 0.65 | 70 | 0.49 |

The samples containing Comparison Couplers (q) and (r) show a larger loss in sensitivity and a decrease in gamma during storage under moist and high temperature conditions (45° C., 80% RH for 4 days), while in the samples containing Compounds (26) and (27) of the present invention, these properties are substantially unchanged and good moisture and heat resistance is observed.

EXAMPLE 13

On a cellulose triacetate film support were coated layers having the compositions set forth below to prepare a multilayer color light-sensitive material. The compound designated with an asterisk (*) are the same compounds as used in Examples 10 and 11.

First Layer: Antihalation Layer (AHL)

Coupler (q)

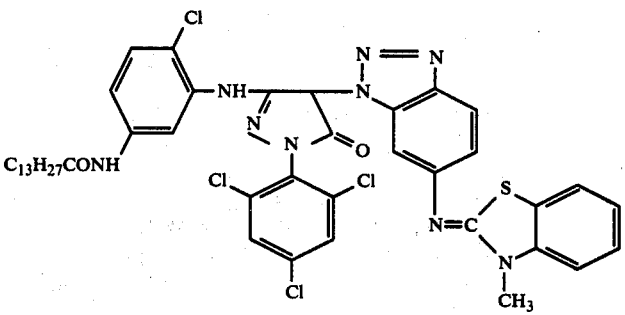

Coupler (r)

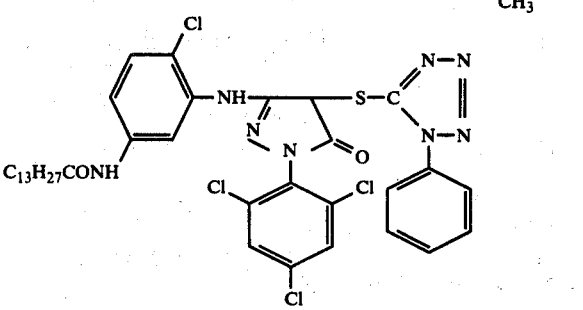

These samples were stored for 4 days under room temperature conditions (20° C., 70% RH) and under conditions of 45° C., 80% RH and then stepwise exposed with white light and processed in the same manner as described in Example 10. After processing, the optical densities to green light of these samples were A gelatin layer containing black colloidal silver (0.2 mg/m²)

Second Layer: Intermediate Layer (ML)

A gelatin layer containing a dispersion of 2,5-di-tert-octylhydroquinone (0.05 g/m²)

Third Layer: First Red-Sensitive Emulsion Layer (RL$_1$)

A silver iodobromide emulsion (iodide content: 5 mol%) . . . silver coated amount 2.0 g/m²

Sensitizing Dye (I)* . . . 6 × 10$^{-5}$ mol per mol of silver

Sensitizing Dye (II)* . . . 1.5 × 10$^{-5}$ mol per mol of silver

Coupler (j)* . . . 0.04 mol per mol of silver
Coupler (s) . . . 0.0015 mol per mol of silver
Coupler (t) . . . 0.0015 mol per mol of silver
Compound (50) described above . . . 0.002 mol per mol of silver Fourth Layer: Second Red-Sensitive Emulsion Layer (RL$_2$)

A silver iodobromide emulsion (iodide content: 4 mol%) . . . silver coated amount 1.7 g/m²

Sensitizing Dye (I)* . . . 3 × 10$^{-5}$ mol per mol of silver

Sensitizing Dye (II)* . . . 1.2 × 10$^{-5}$ mol per mol of silver

Coupler (j)* . . . 0.015 mol per mol of silver
Coupler (s) . . . 0.0006 mol per mol of silver
Coupler (t) . . . 0.0006 mol per mol of silver
Compound (50) described above . . . 0.0003 mol per mol of silver Fifth Layer: Intermediate Layer (ML)

Same as the Second Layer

Sixth Layer: First Green-Sensitive Emulsion Layer (GL$_1$)

A silver iodobromide emulsion (iodide content: 4 mol%) . . . silver coated amount 1.8 g/m²

Sensitizing Dye (III)* . . . 3 × 10$^{-5}$ mol per mol of silver

Sensitizing Dye (IV)* . . . 1 × 10$^{-5}$ mol per mol of silver

Coupler (k) . . . 0.05 mol per mol of silver
Coupler (u) . . . 0.008 mol per mol of silver
Compound (26) described above . . . 0.0023 mol per mol of silver Seventh Layer: Second Green-Sensitive Emulsion Layer (GL$_2$)

A silver iodobromide emulsion (iodide content: 5 mol%) . . . silver coated amount 1.8 g/m²

Sensitizing Dye (III)* . . . 2.5 × 10$^{-5}$ mol per mol of silver

Sensitizing Dye (IV)* . . . 0.8 × 10$^{-5}$ mol per mol of silver

Coupler (k) . . . 0.015 mol per mol of silver
Coupler (u) . . . 0.002 mol per mol of silver
Compound (26) described above . . . 0.0003 mol per mol of silver Eighth Layer: Yellow Filter Layer (YEL)

A gelatin layer containing yellow colloidal silver (0.1 g/m²) and a dispersion of 2,5-di-tert-octylhydroquinone (0.1 g/m²)

Ninth Layer: First Blue-Sensitive Emulsion Layer (BL$_1$)

A silver iodobromide emulsion (iodide content: 6 mol%) . . . silver coated amount 0.8 g/m²

Coupler (l)* . . . 0.25 mol per mol of silver

Compound (6) described above . . . 0.0025 mol per mol of silver

Tenth Layer: Second Blue-Sensitive Emulsion Layer (BL$_2$)

A silver iodobromide emulsion (iodide content: 6 mol%) . . . silver coated amount 0.9 g/m²

Coupler (l)* . . . 0.06 mol per mol of silver

Eleventh Layer: Protective Layer (PL)

A gelatin layer containing an ultra-fine grain silver iodobromide emulsion (containing 0.06 mol of silver per kg of emulsion, having an iodide content of 1.4 mol%, and having an average grain size of 0.03μ), and polymethyl methacrylate particles (having a diameter of about 1.5μ) . . . silver coated amount 2.3 g/m².

A gelatin hardener and a surface active agent as described in Example 11, in addition to the above-described components, was incorporated in each of the layers.

The thus prepared sample was designated Sample 401.

Samples 402 and 403

These samples were prepared in the same manner as Sample 401 except that the compounds set forth in Table 13 below were used in place of Compounds (6), (26) and (50) of Sample 401, respectively. The amounts of the compounds set forth in Table 13 are shown as mol per mol of silver.

TABLE 13

| Layer Added | Sample 402 Compound | Amount | Sample 403 Compound | Amount |
|---|---|---|---|---|
| RL$_1$ | Compound (42) | 0.002 | Coupler (u) (for comparison) | 0.002 |
| RL$_2$ | Compound (42) | 0.0003 | Coupler (v) (for comparison) | 0.0003 |
| GL$_1$ | Compound (27) | 0.0025 | Coupler (q)* (for comparison) | 0.002 |
| GL$_2$ | Compound (27) | 0.0004 | Coupler (q)* (for comparison) | 0.00033 |
| BL$_1$ | Compound (5) | 0.003 | Coupler (w) (for comparison) | 0.012 |

The comparison couplers used are the development inhibitor releasing compounds described in U.S. Pat. No. 3,227,554.

The samples thus prepared were exposed stepwise with white light and subjected to sensitometry as described in Example 10. The sensitivity and gradation in each emulsion layer of Samples 401 to 403 were approximately equal.

The evaluations of the edge effects and the RMS graininess of these samples were carried out in the same manner as described in Example 11. The results obtained are shown in Table 14 below.

The couplers used for the preparation of these samples were as follows.

Coupler (s): 1-Hydroxy-4-[2-(2-hexyldecyloxycarbonyl)phenylazo]-2-[N-(1-naphthyl)]naphthamide Coupler (t): 1-Hydroxy-4-[4-(ethyloxycarbonyl)phenylazo]-2-(N-dodecyl)naphthamide Coupler (u): 1-(2,4,6-Trichlorophenyl)-3-[(2-chloro-5-hexadecanamido)anilino]-4-(4-tert-butyramido)-phenylazo-5-oxo-2-pyrazoline Coupler (v): 1-Hydroxy-4-(1-phenyltetrazol-5-ylthio)-N-(2-tetradecyloxy)-2-naphthanilide Coupler (w): α-(1-Phenyltetrazol-5-ylthio)-α-pivaloyl-2-chloro-5-[α-(2,4-di-tert-amylphenoxy)-butyramido]-acetanilide

TABLE 14

| Sample No. | Light for Measurement | Edge Effects $(D_1 - D_2)/D_1$ | RMS Graininess $D = 0.5$ | RMS Graininess $D = 1.5$ | Interlayer Effects $\gamma G/\gamma R$ | $\gamma G/\gamma B$ | $\gamma R/\gamma G$ | $\gamma B/\gamma G$ |
|---|---|---|---|---|---|---|---|---|
| 401 | Blue light | 0.30 | 0.063 | 0.068 | | | | |
| | Green light | 0.48 | 0.036 | 0.034 | −0.38 | −0.21 | −0.39 | −0.30 |
| | Red light | 0.52 | 0.033 | 0.030 | | | | |
| 402 | Blue light | 0.25 | 0.068 | 0.070 | | | | |
| | Green light | 0.39 | 0.039 | 0.035 | −0.28 | −0.13 | −0.25 | −0.21 |
| | Red light | 0.41 | 0.035 | 0.032 | | | | |
| 403 | Blue light | 0.09 | 0.072 | 0.077 | | | | |
| | Green light | 0.16 | 0.046 | 0.043 | −0.12 | −0.05 | −0.18 | −0.14 |
| | Red light | 0.20 | 0.040 | 0.039 | | | | |

Interlayer effects: $\gamma A/\gamma B$ designates the amount of interlayer effects from Layer B to Layer A as shown in Example 12 and the smaller the value, i.e., the greater absolute value of minus shows larger interlayer effects.

It is apparent from the results shown above that Samples 401 and 402 with the compounds of the present invention show greater edge effects, effects of reducing the graininess and interlayer effects and thus have superior properties as compared with Sample 403 containing a comparison coupler. In particular, Sample 401 containing Compounds (6), (26) and (50) exhibits extremely superior properties.

Furthermore, these samples were cut into films of a 35 mm size and photographed to form negative films. Color prints were prepared by printing the negative films using an enlarging technique. The color print obtained using Samples 401 and 402 had finer graininess, particularly in the low density area and sharper images ranging from low density to high density in comparison with Sample 403. Also, color reproductions of green and red colors were particularly superior. These features were particularly remarkable in Sample 401.

While the invention has been described in detail and with reference to specific embodiments thereof, it will be apparent to one skilled in the art that various changes and modifications can be made therein without departing from the spirit and scope thereof.

What is claimed is:

1. A color photographic element comprising a silver halide emulsion containing a two equivalent photographic coupler having a releasable group substituted at the coupling position of said coupler and represented by the following general formula:

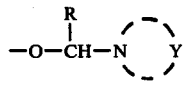

wherein R represents a hydrogen atom, a halogen atom, an alkyl group, an alkenyl group, an aralkyl group, an aralkenyl group, an aryl group or a heterocyclic group; and Y represents the non-metallic atoms necessary to form a 5- or 7-membered ring together with the N atom forming a part thereof.

2. The element as claimed in claim 1, wherein said coupler is represented by the following general formula (I):

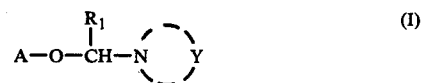

wherein A represents a coupler residue; $R_1$ represents a hydrogen atom, a halogen atom, an alkyl group, an alkenyl group, an aralkyl group, an aralkenyl group, an aryl group or a heterocyclic group; and Y represents the non-metallic atoms necessary to form a 5- or 7-membered ring together with the N atom forming a part thereof.

3. The element as claimed in claim 2, wherein said coupler residue A is a residue of a four equivalent coupler in which one hydrogen atom on the coupling position is replaced by said releasable group.

4. The element as claimed in claim 3, wherein said coupler residue is a residue of a pivaloylacetanilide coupler, a benzoylacetanilide coupler or a malondiamide coupler.

5. The element as claimed in claim 3, wherin said coupler residue is a residue of a 5-oxo-2-pyrazoline coupler or a pyrazolo-[1,5-a]-benzimidazole coupler.

6. The element as claimed in claim 3, wherein said coupler residue is a residue of a 2-acylaminophenol coupler or an α-naphthol coupler.

7. The element as claimed in claim 2, wherein $R_1$ is a hydrogen atom.

8. The element as claimed in claim 2, wherein said alkyl group, said alkenyl group, said aralkyl group, and said aralkenyl group each has up to 18 carbon atoms.

9. The element as claimed in claim 2, wherein said aryl group has 6 to 12 carbon atoms.

10. The element as claimed in claim 2, wherein said heterocyclic group is a 5- or 6-membered ring containing, as a hetero atom, one or more of a nitrogen atom, a sulfur atom or an oxygen atom.

11. The element as claimed in claim 2, wherein Y represents the non-metallic atoms necessary to form a cyclic imide group, a cyclic amide group, a cyclic urea group, an imidazole group, a pyrazole group, a triazole group, a sultam group or a cyclic amine group.

12. The element as claimed in claim 2, wherein Y represents the non-metallic atoms necessary to form a cyclic group having the following general formula:

13. The element as claimed in claim 2, wherein Y represents the non-metallic atoms necessary to form a cyclic group having the following general formula:

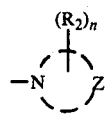

wherein Z has the same meaning as Y; $R_2$ represents a halogen atom, a hydroxy group, a carboxy group, an alkoxycarbonyl group, a nitro group, a cyano group, an aryl group, an alkoxy group, an aryloxy group, an acyl group, an acylamino group, a sulfo group, a sulfamoyl group, a sulfonamido group, a carbamoyl group, an imido group, an imino group, a ureido group, a urethane group, an alkylthio group, an amino group or an alkyl group; and n represents 0 to 5.

14. The element as claimed in claim 13, wherein said cyclic group is a benzotriazole ring having on the benzene ring thereof a group represented by the following general formula:

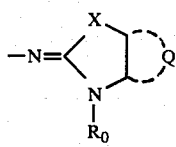

wherein $R_0$ represents an aliphatic group, an aralkyl group or an aromatic group; X represents an oxygen atom; a sulfur atom or an $R_0$—N< group; and Q represents the atoms necessary to form an aromatic ring.

15. The element as claimed in claim 2, wherein said coupler residue A is represented by the general formulae (III), (IV), (V), (VI), or (VII):

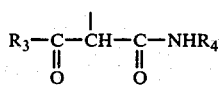

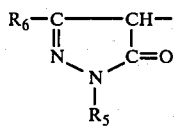

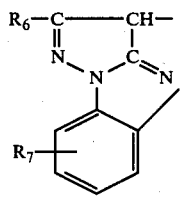

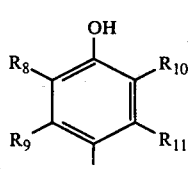

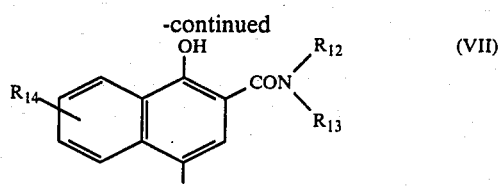

wherein $R_3$ represents an aliphatic group, an aromatic group, or a heterocyclic group; $R_4$ represents an aromatic group or a heterocyclic group; $R_5$ represents a group having up to 32 carbon atoms selected from the group consisting of an alkyl group, an alkenyl group, a cycloalkyl group, an aralkyl group, a cycloalkenyl group, an aryl group and a heterocyclic group; $R_6$ represents a halogen atom or has up to 32 carbon atoms and represents an aliphatic group, an alkoxy group, an acylamino group, an N-alkylacylamino group, a ureido group, a urethane group, an arylamino group, an alkylamino group, a cycloalkylamino group, a heterocyclic amino group, an alkylsulfonamido group or an arylsulfonamido group; $R_7$ has up to 32 carbon atoms and represents a hydrogen atom, an aliphatic group, an aryloxy group, an aryl group, a heterocyclic group, a halogen atom, a cyano group, an alkoxy group, a carboxy group, an alkoxycarbonyl group, a sulfo group, a sulfamoyl group, a carbamoyl group, an acylamino group, a diacylamino group, a ureido group, a urethane group, a sulfonamido group, an arylsulfonyl group, an alkylsulfonyl group, an arylthio group, an alkylthio group, an alkylamino group, a dialkylamino group, a hydroxy group, or a mercapto group; $R_8$, $R_{11}$ and $R_{14}$ each has up to 32 carbon atoms and represents an aliphatic group, an alkoxy group, an alkylthio group, an acylamino group, a diacylamino group, a ureido group, a urethane group, or a sulfonamido group; $R_9$ and $R_{10}$ each represents a hydrogen atom, a halogen atom, an alkyl group having 1 to 10 carbon atoms, or an alkoxy group having 1 to 10 carbon atoms; and $R_{12}$ and $R_{13}$ each represents a halogen atom, an aliphatic group or an aryl group.

16. A method of forming color photographic images which comprises developing an imagewise exposed silver halide photographic emulsion carried on a support with an aromatic primary amine developing agent in the presence of a two equivalent photographic coupler having a releasable group substituted at the coupling position of said coupler and represented by the following general formula:

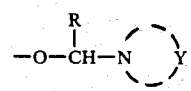

wherein R represents a hydrogen atom, a halogen atom, an alkyl group, an alkenyl group, an aralkyl group, an aralkenyl group, an aryl group or a heterocyclic group; and Y represents the non-metallic atoms necessary to form a 5- or 7-membered ring together with the N atom forming a part thereof said aromatic primary amine developing agent, after the oxidation thereof, coupling with said coupler.

17. The element as claimed in claim 1, wherein the coupler is a cyan dye-forming coupler.

18. The element as claimed in claim 1, wherein the coupler is a non-diffusible coupler which forms a non-diffusible dye by coupling with an oxidation product of an aromatic primary amine developing agent.

19. The element as claimed in claim 1, wherein said releasable group, following coupling, cleaves according to the following reaction scheme:

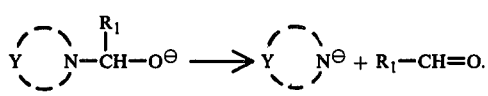

20. The element as claimed in claim 1, wherein R represents a hydrogen atom.

21. The element as claimed in claim 1, wherein R represents a halogen atom.

22. The element as claimed in claim 1, wherein R represents an alkyl group.

23. The element as claimed in claim 1, wherein R represents an aryl group.

24. The element as claimed in claim 1, wherein R represents a heterocyclic group.

25. The element as claimed in claim 1, wherein said coupler has the formula:

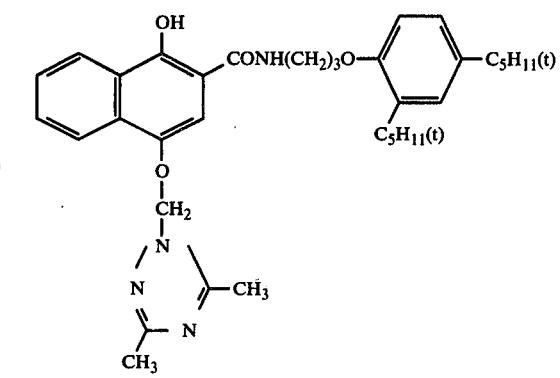

* * * * *